(12) United States Patent
Virr et al.

(10) Patent No.: US 7,137,388 B2
(45) Date of Patent: Nov. 21, 2006

(54) AIR PRESSURE SIGNAL MONITORING IN APPARATUS FOR TREATING SLEEP DISORDERED BREATHING

(75) Inventors: Alexander Virr, Balmain (AU); Ian Malcolm Smith, Westleigh (AU); Perry David Lithgow, Glenwood (AU); Richard Llewelyn Jones, Hornsby Heights (AU); Andrew Cheung, Burwood (AU)

(73) Assignee: ResMed Limited, North Ryde (AU)

( * ) Notice: Subject to any disclaimer, the term of this patent is extended or adjusted under 35 U.S.C. 154(b) by 10 days.

(21) Appl. No.: 10/467,304

(22) PCT Filed: Feb. 14, 2002

(86) PCT No.: PCT/AU02/00156

§ 371 (c)(1),
(2), (4) Date: Aug. 7, 2003

(87) PCT Pub. No.: WO02/066107

PCT Pub. Date: Aug. 29, 2002

(65) Prior Publication Data

US 2004/0055597 A1 Mar. 25, 2004

(30) Foreign Application Priority Data

Feb. 16, 2001 (AU) ..................... PR3117
Aug. 27, 2001 (AU) ..................... PR7287

(51) Int. Cl.
*A61M 11/00* (2006.01)
*A61M 15/00* (2006.01)
*A61M 16/00* (2006.01)
(52) U.S. Cl. .......................... 128/203.17; 128/200.14; 128/200.18; 128/200.21; 128/203.12; 128/203.14; 128/203.16; 128/203.26; 128/203.27

(58) Field of Classification Search ........... 128/200.14, 128/200.18, 200.21, 203.12, 203.14, 203.16, 128/203.17, 203.26, 203.27, 204.14, 204.17, 128/205.23
See application file for complete search history.

(56) References Cited

U.S. PATENT DOCUMENTS

| 4,657,713 | A | * | 4/1987 | Miller | 261/142 |
| 4,753,758 | A | * | 6/1988 | Miller | 261/139 |
| 4,906,417 | A | * | 3/1990 | Gentry | 261/30 |
| 4,913,140 | A | * | 4/1990 | Orec et al. | 128/203.16 |
| 4,921,642 | A | * | 5/1990 | LaTorraca | 261/142 |

(Continued)

FOREIGN PATENT DOCUMENTS

WO 98/57691 12/1998

(Continued)

OTHER PUBLICATIONS

Verified Translation of PCT/EP00/07602 (WO 01/10489).

(Continued)

*Primary Examiner*—Henry Bennett
*Assistant Examiner*—Nihir Patel
(74) *Attorney, Agent, or Firm*—Nixon & Vanderhye P.C.

(57) ABSTRACT

A humidifier is provided including a first humidifier part, a second humidifier part connectable with the first humidifier part, and a sealing gasket disposed between the first and second humidifier parts. The second humidifier part is configured to hold a volume of liquid therein and the first and second humidifier parts and the sealing gasket define first and second internal passages within the humidifier. The first passage is disposed so as to be exposed to a surface of the volume of liquid and the second passage is isolated from at least one of the first passage and the surface of the volume of liquid. The second passage is configured to communicate with a pressure and/or sound sensing device.

23 Claims, 21 Drawing Sheets

U.S. PATENT DOCUMENTS

| | | | |
|---|---|---|---|
| 4,993,411 A * | 2/1991 | Callaway | 128/204.14 |
| 5,231,979 A * | 8/1993 | Rose et al. | 128/204.14 |
| 5,445,143 A * | 8/1995 | Sims | 128/203.26 |
| 5,537,997 A | 7/1996 | Mechlenburg et al. | |
| 5,558,084 A * | 9/1996 | Daniell et al. | 128/203.17 |
| 5,564,415 A * | 10/1996 | Dobson et al. | 128/204.14 |
| 5,598,837 A * | 2/1997 | Sirianne et al. | 128/204.14 |
| 5,655,522 A * | 8/1997 | Mechlenburg et al. | 128/203.12 |
| 5,673,687 A * | 10/1997 | Dobson et al. | 128/204.14 |
| 5,916,493 A | 6/1999 | Miller et al. | |
| 5,943,473 A * | 8/1999 | Levine | 392/401 |
| 6,131,571 A | 10/2000 | Lampotang et al. | |
| 6,135,432 A | 10/2000 | Hebblewhite et al. | |
| D454,393 S * | 3/2002 | Lynch et al. | D24/110 |
| 6,435,180 B1 * | 8/2002 | Hewson et al. | 128/204.18 |
| D467,335 S * | 12/2002 | Lithgow et al. | D24/110 |
| D468,011 S * | 12/2002 | Lynch et al. | D24/110 |
| D468,017 S * | 12/2002 | McCombs | D24/164 |
| 6,554,260 B1 * | 4/2003 | Lipscombe et al. | 261/142 |
| D487,311 S * | 3/2004 | Lithgow et al. | D24/110 |
| 6,718,974 B1 * | 4/2004 | Moberg | 128/204.14 |
| D493,520 S * | 7/2004 | Bertinetti et al. | D24/110 |
| D493,884 S * | 8/2004 | Virr et al. | D24/110 |
| 6,772,999 B1 * | 8/2004 | Lipscombe et al. | 261/131 |
| D498,527 S * | 11/2004 | Virr et al. | D24/110 |
| 6,827,340 B1 * | 12/2004 | Austin et al. | 261/119.1 |
| 6,874,771 B1 * | 4/2005 | Birdsell et al. | 261/131 |
| 6,935,337 B1 * | 8/2005 | Virr et al. | 128/203.16 |
| 2002/0020930 A1 | 2/2002 | Austin et al. | |

FOREIGN PATENT DOCUMENTS

| | | |
|---|---|---|
| WO | 00/32261 | 6/2000 |
| WO | WO 01/10489 A2 * | 2/2001 |
| WO | WO 01/10489 | 3/2001 |

OTHER PUBLICATIONS

European Search Report, Appln. No. EP 02711641 (Mar. 21, 2005).
New Zealand Patent Office Examination Report from corresponding New Zealand application, Oct. 10, 2003, 2 pgs.

* cited by examiner

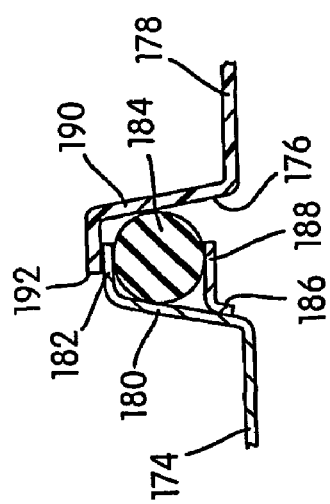
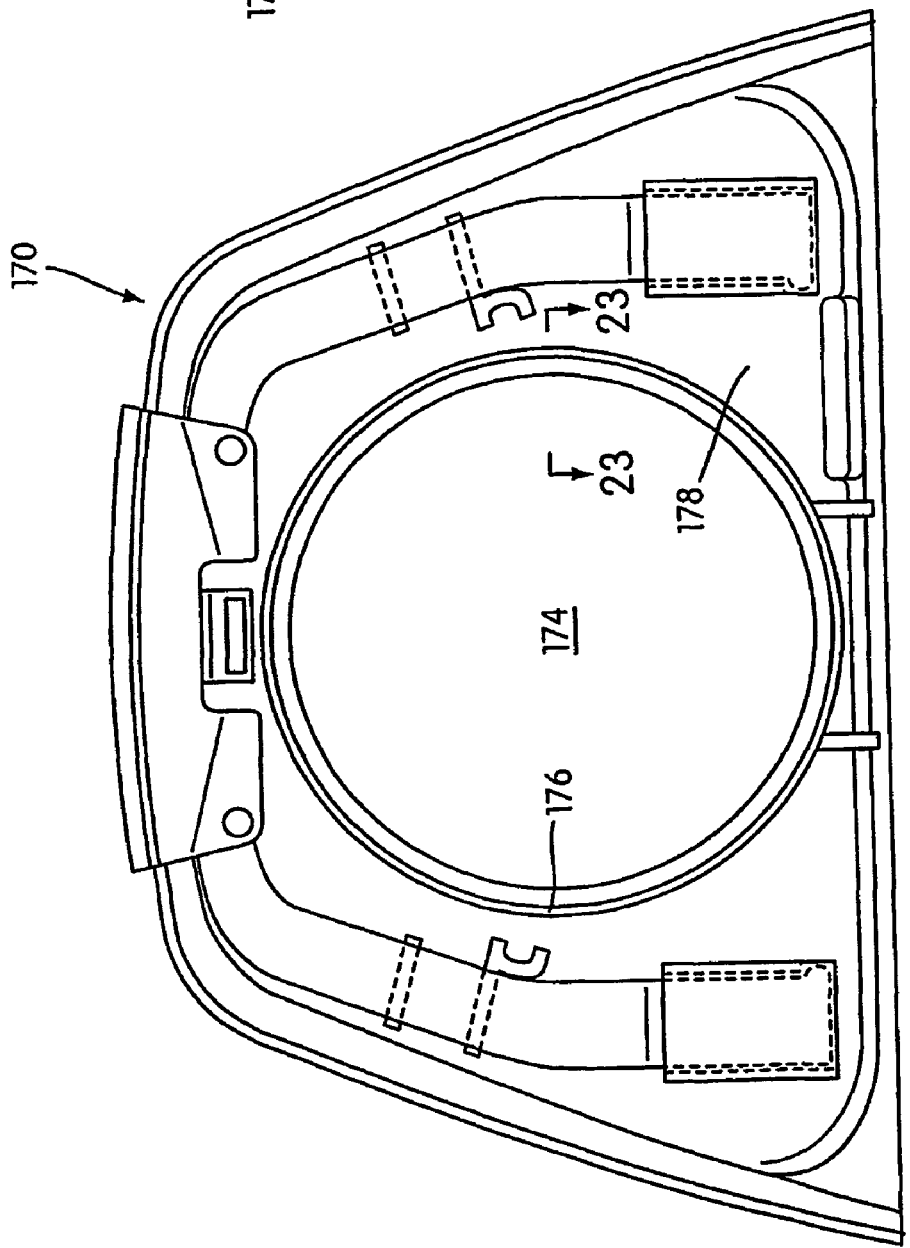

AIR PRESSURE SIGNAL MONITORING IN APPARATUS FOR TREATING SLEEP DISORDERED BREATHING

This application is the US national phase of international application PCT/AU02/00156 filed 14 Feb. 2002, which designated the US.

The present application claims priority to Australian Provisional Applications PR3117, filed on Feb. 16, 2001 and PR7287, filed on Aug. 27, 2001, the specifications and drawings of which are incorporated by reference in their entireties.

The invention relates to the monitoring of air pressure signals in apparatus for treating sleep disorder breathing.

Obstructive Sleep Apnea (OSA) may be treated by the application of nasal Continuous Positive Airway Pressure (CPAP). CPAP treatment provides pressurized air or other breathable gas to the entrance of a patient's airways at a pressure elevated above atmospheric pressure. It is also known for the level of treatment pressure to vary from breath to breath in accordance with patient need, that form of CPAP being known as "automatically adjusting nasal CPAP treatment." U.S. Pat. No. 5,704,345 describes a method and apparatus for continuously adjusting the CPAP pressure while monitoring patient respiration air flow and pressure via a pressure sensor communicated with the supply conduit extending between the mask and blower. In particular, pressure sensor is in communication with the supply conduit via an additional segment of conduit extending between the supply conduit and pressure sensor.

Alternatively, as illustrated schematically in FIG. 23, a CPAP apparatus, indicated at 500 may include a blower 502 connected to a mask 504 via supply conduit 506 and a pressure transducer 508 is in communication with the mask 504 itself via a monitoring conduit 510. The pressure transducer 508 is located within the CPAP apparatus 500 and is in communication with a CPU 512. The CPU 512 is connected to the blower 502 in such a manner to be capable of controlling an output thereof based on parameters sensed by the pressure transducer 508.

In one embodiment of U.S. Pat. No. 5,245,995, illustrated schematically in FIG. 24, a pressure transducer 514 is incorporated into the mask 504 itself and is in communication with the CPU 512 via a wire 516. In another embodiment of U.S. Pat. No. 5,245,995, a microphone is connected to the mask and in communication with the CPU via a wire.

Some of the embodiments described above and disclosed in U.S. Pat. No. 5,704,345 and U.S. Pat. No. 5,245,995 may utilize additional tubing or wiring to connect the monitoring device (e.g., pressure transducer and/or microphone) on the mask or supply conduit to the controller within the CPAP apparatus. These arrangements are disadvantageous, however, since the additional tubes or wires are difficult to manipulate and can tangle. Additionally, embodiments incorporating a monitoring device into the mask itself are often uncomfortable for the users.

Other CPAP apparatus embodiments utilize a monitoring device within the blower itself, such as schematically illustrated in FIG. 25. Due to the relative proximity between the blower 502 and CPU 512, the monitoring device 508 (e.g., pressure transducer) may be communicated with the CPU 512 without necessitating use of superfluous lengths of additional tubing. However, signals measured in the blower 502 must be corrected with a corresponding correction factor for any changes which may occur in the signal's communication from the mask 504, along the supply conduit 506 to the blower 502. For example, when using an accessory such as a humidifier indicated at 520 in FIG. 26, which may behave as a muffler attenuating the AC component of the pressure signal, the CPU 512 may not be able to correct for the added attenuation, for example, if the level of attenuation is variable, such as due to varying levels of liquid within the humidifier. Alternatively, the correction factor may need to be altered for use with an accessory such as a humidifier. However, continued correction for accessories may degrade the accuracy of the corrected value.

The use of an accessory such as a humidifier may be desirable, however. Some patients find treatment more comfortable if the air from the blower outlet is humidified, which can be achieved by placing a humidifier in between the blower and the supply conduit. The humidifier includes a chamber containing a volume of water, which water acts to humidify the breathable air flowing through the humidifier. However as discussed above, the presence of the humidifier in the air flow path alters and may degrade the air pressure signal which can be detected by transducers in the blower.

One embodiment of U.S. Pat. No. 5,537,997, schematically illustrated in FIG. 27, discloses using a second conduit 522 to connect a pressure transducer 508 inside the CPAP apparatus 500 to a point in the supply conduit 506 between the humidifier 520 and the mask 504. However, the second conduit 522 represents additional componentry which can be an inconvenience for the patient and the clinician administering use of the CPAP apparatus. In U.S. Pat. No. 5,537,997, the second conduit 522 extends externally of the humidifier 520. Such extra tubing may tangle easily and become disconnected. This is disadvantageous, since typical patients have poor dexterity and the pressure and/or snore signal is used to maintain the intended therapy.

Apparatuses utilizing additional tubing are also disadvantageous, as cleaning and disinfection may be difficult. Disinfection prevents cross-infection of patients using a shared blower.

Another attempt to diminish signal attenuation is schematically illustrated in FIGS. 28 and 29 and are disclosed in U.S. patent application Ser. No. 09/099,665, incorporated herein by reference. In the embodiment of FIGS. 28–29, the humidifier can be removed and replaced with appropriate tubing and/or a conduit. FIG. 29 shows the humidifier after its removal, with the appropriate tubing/conduit in its place. Like he embodiment of FIG. 27, the pressure transducer in FIG. 28 is between the humidifier and the mask, which avoids routing the signal through the humidifier.

It is one aspect of the present invention to substantially overcome or at least ameliorate the above disadvantages or at least provide a useful alternative.

It is another aspect to provide a humidifier for a CPAP apparatus with fist and second passages, one of which avoids the degradation of measurement signals typically incurred due to is attenuation within the humidifier.

It is another aspect to provide a humidifier for a CPAP apparatus with first and second passages, wherein the first and second passages are formed integrally with the humidifier.

It is yet another aspect to provide a humidifier for a CPAP apparatus which has separable componentry that separates to substantially entirely expose the interiors of the components.

It is another aspect to provide a humidifier for a CPAP apparatus that is relatively easier to manufacture than prior art humidifiers.

It is another aspect to provide a humidifier for a CPAP apparatus that is relatively easier to assemble than prior art humidifiers.

It is another aspect to provide a humidifier for a CPAP apparatus that is relatively easier to disassemble than prior art humidifiers.

One embodiment of the present invention includes a humidifier including a first humidifier part, a second humidifier part connectable with the first humidifier part, and a sealing gasket disposed between the first and second humidifier parts. The second humidifier part is configured to hold a volume of liquid therein and the first and second humidifier parts and the sealing gasket define first and second internal passages within the humidifier. The first passage is disposed so as to be exposed to a surface of the volume of liquid and the second passage is isolated from at least one of the first passage and the surface of the volume of liquid. The second passage is configured to communicated with a pressure and/or sound sensing device.

In this manner, a pressure signal may be detected within the isolated second passage without degrading the signal by attenuation within the first passage.

It is contemplated that the first and second humidifier parts may be separable from one another in a manner such that walls of the first and second internal passages may be substantially entirely exposed.

In this manner, the first and second humidifier parts may be separated so as to substantially entirely expose the interiors thereof in order to easily clean and disinfect the interiors.

A portion of an internal surface of the first humidifier part may define at least one internal wall of the second internal passage.

The first humidifier part may include a top wall, a peripherally extending side wall extending downwardly from the top wall, and an internal wall structure extending downwardly from the top wall generally parallel to and inwardly spaced from the peripherally extending side wall. The internal wall structure, portions of the top wall, and portions of the peripherally extending side walls may define corresponding internal walls of the internal passage.

A portion of a surface of the sealing member may define a corresponding internal wall of the internal passage.

The first humidifier part may include first and second inlet tubes and an outlet tube, the first inlet tube and outlet tube may be communicated with the first internal passage, and the second inlet tube and the outlet tube may be communicated with the second internal passage.

The outlet tube may extend from the internal wall structure of the first humidifier part in such a manner to be communicated with the first internal passage to outside of the humidifier and the second internal passage may be communicated with the outlet tube via at least one aperture formed in the outlet tube.

The at least one aperture may be provided by a pair of apertures.

The first inlet tube may extend from the internal wall structure of the first humidifier part in such a manner to be communicated with the first internal passage to outside of the humidifier, and the second inlet tube may extend from the peripherally extending side wall of the first humidifier part in such a manner to be communicated with the second internal passage to the aperture within the outlet tube.

The second inlet tube may be coaxial with and surround the first inlet tube.

The first and second humidifier parts may be formed from a relatively rigid polymer material and the sealing gasket may be formed from a relatively resilient material.

It is also contemplated that the humidifier may include a heater configured to raise a temperature of the volume of liquid within the humidifier.

Another embodiment of the present invention includes a CPAP apparatus including a humidifier of the embodiment described above.

Another embodiment of the present invention includes a method of determining pressure within a conduit supplying breathable gas from a CPAP apparatus to a patient mask. The method includes providing a humidifier with first and second internal passages therein. The first passage is disposed within the humidifier so as to be exposed to a surface of a volume of liquid present within the humidifier and the second passage is isolated from the first passage. The method includes supplying the breathable gas to a first inlet tube of the humidifier in communication with the first internal passage so that breathable gas flowing therethrough is humidified by contact with the volume of liquid and is communicated with an outlet tube of the humidifier. Furthermore, the method includes providing an aperture within the outlet tube in communication with the second internal passage and measuring a pressure within the second internal passage to determine pressure within the outlet tube.

Although certain embodiments of the invention are illustrated and described herein as having certain features, one skilled in the art would recognize that alternative embodiments of the invention could be provided based on at least one or more features, either individually or in combination, of the illustrated and described embodiments.

The benefits of the present invention will be readily appreciated and understood from consideration of the following detailed description of embodiments of this invention, when taken with the accompanying drawings, wherein:

FIG. 20 is a bottom view of the humidifier shown in FIG. 18;

FIG. 21 is a cross-sectional view taken along line 23—23 in FIG. 20;

Figure 1:
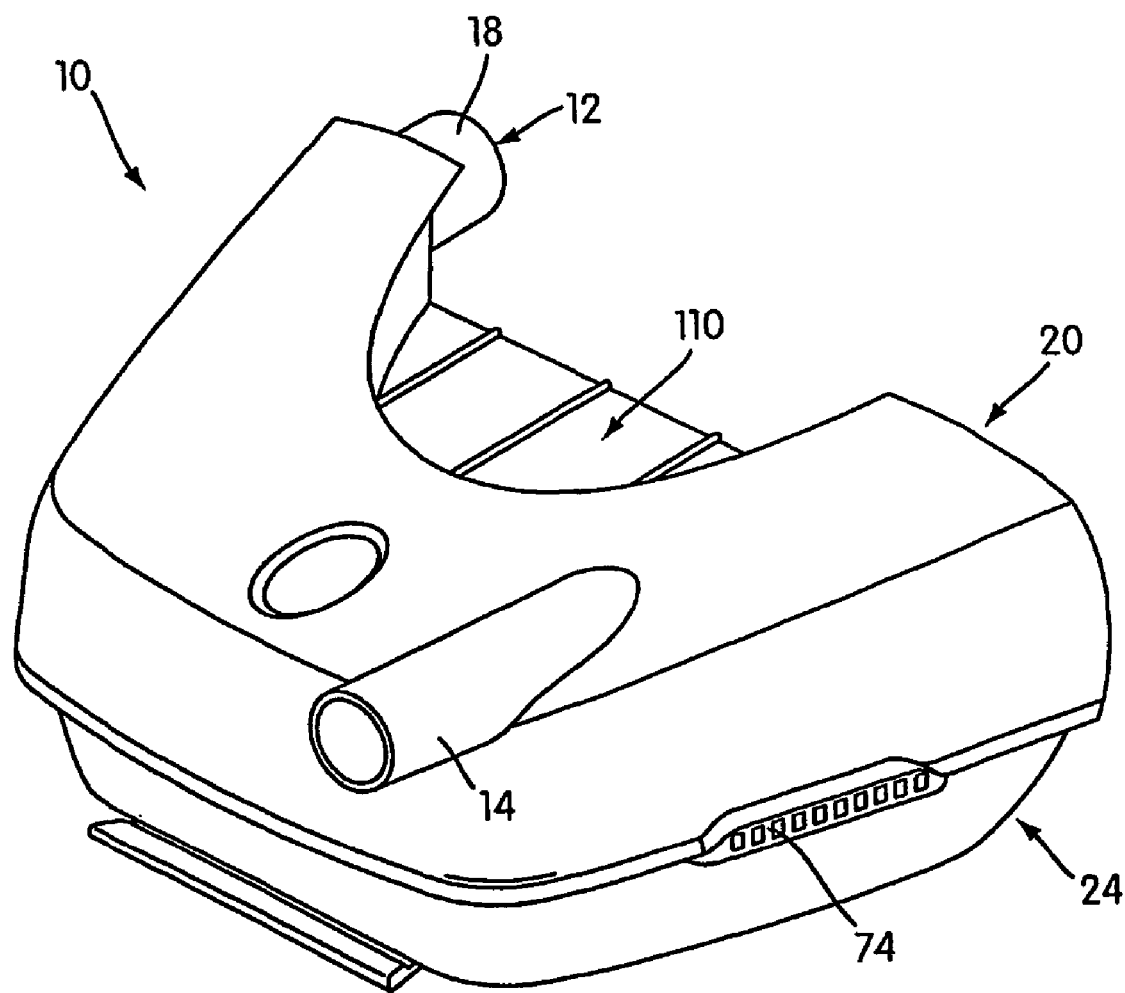
FIG. 1 is a perspective view of a humidifier according to one embodiment of the present invention.

FIG. 1 shows one contemplated embodiment of a humidifier 10 according to the present invention. The humidifier 10 includes an inlet 12 and an outlet 14, both being communicated with an interior of the humidifier 10. The humidifier inlet 12 is adapted for detachable connection to an output of a CPAP or NIPPV (Non-invasive Positive Pressure Ventilation) apparatus (not shown), which includes a blower for providing a supply of pressurized breathable gas to the humidifier 10. The outlet 14 is connectable to an outlet conduit (not shown) leading to and communicated with a patient, e.g., via a mask, and a monitoring conduit in communication with a pressure and/or sound sensing device (e.g., pressure transducer, microphone, etc.) within the CPAP or NIPPV apparatus. Air from the blower enters the inlet 12 and collects moisture through contact with the water within the humidifier 10, before continuing on to the outlet 14 and to the patient. The humidifier 10 includes a first humidifier part, or top cover 20 and a second humidifier part, or base 24, which are held together, for example, with a pair of sliding retaining clips 74. It is contemplated that the top cover 20 and base 24 may alternatively be secured to one another by, for example, having a snap-fit configuration, or use of other suitable fastening arrangements. Additionally, the top cover 20 may be formed with a recess 110 therein, discussed further below.

Figure 2:
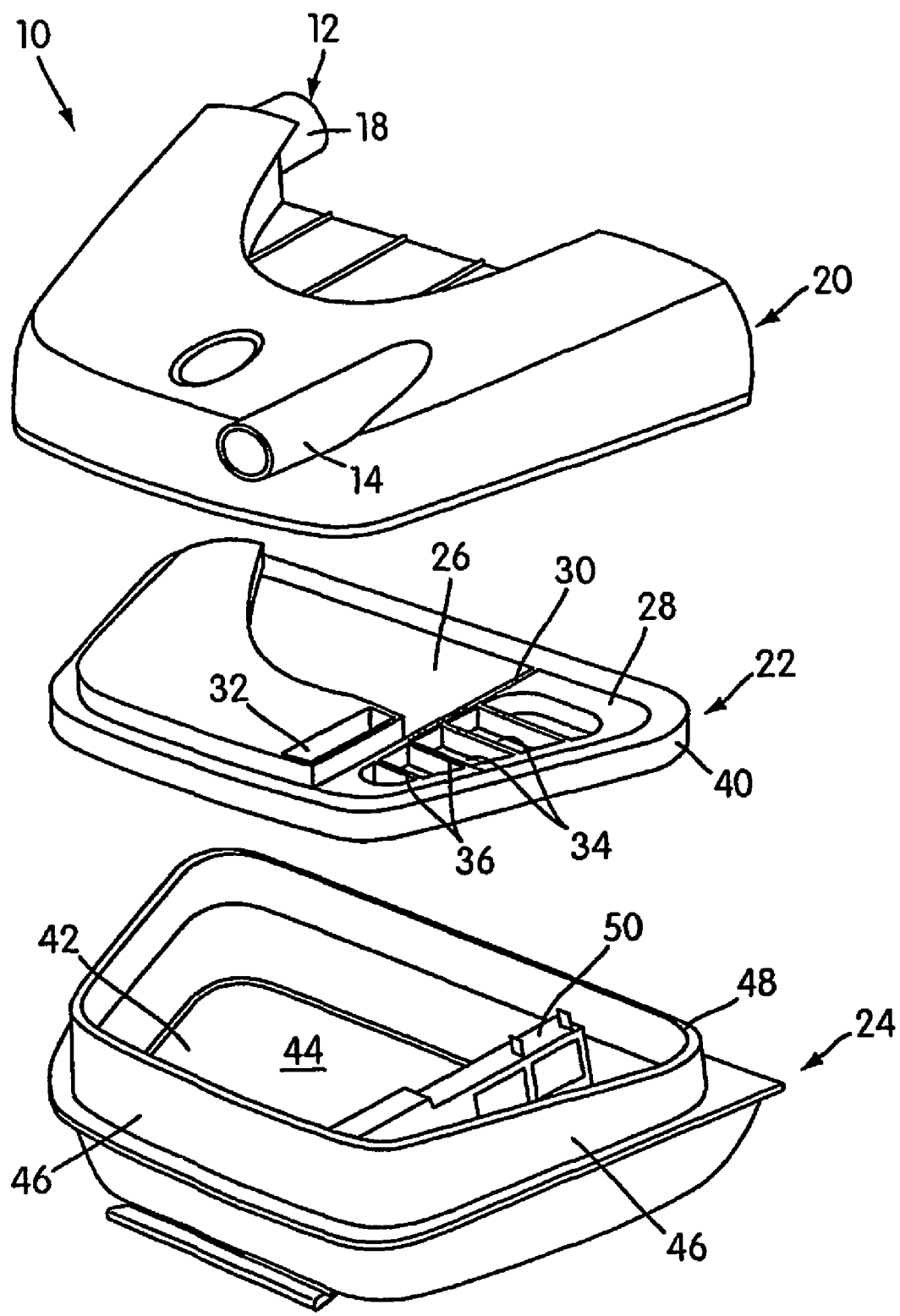
FIG. 2 is an exploded perspective view of the humidifier shown in FIG. 1.

As shown in FIG. 2, the humidifier 10 includes a gasket 22 between the top cover 20 and base 24. The top cover 20 may be formed from a relatively rigid polymer material, such as polysulfone (for example, grade UDEL P1700, manufactured by BP Amoco Polymers) and includes the inlet 12 and the outlet 14. The gasket 22 may be formed of a relatively resilient material, such as silicone rubber (for example, SILASTIC 94-595-HC, manufactured by Dow Corning), and is divided into first and second sections 26 and 28 by a channel structure 30. The first section 26 may include a first vertically extending aperture 32. The second section 28 may include a plurality of second vertically extending apertures 34, which are separated from each other by ribs 36. The gasket 22 may include a sealing flange 40 formed about a periphery thereof.

It is contemplated that the base 24 may be formed from a relatively rigid polymer material, such as that used to form the top cover 20, and includes a receptacle 42 formed therewithin, a bottom wall 44, side walls 46 extending upwardly from the bottom wall 44, and a ledge portion 48. The base 24 may also include a removable bridge structure 50.

Figure 3:
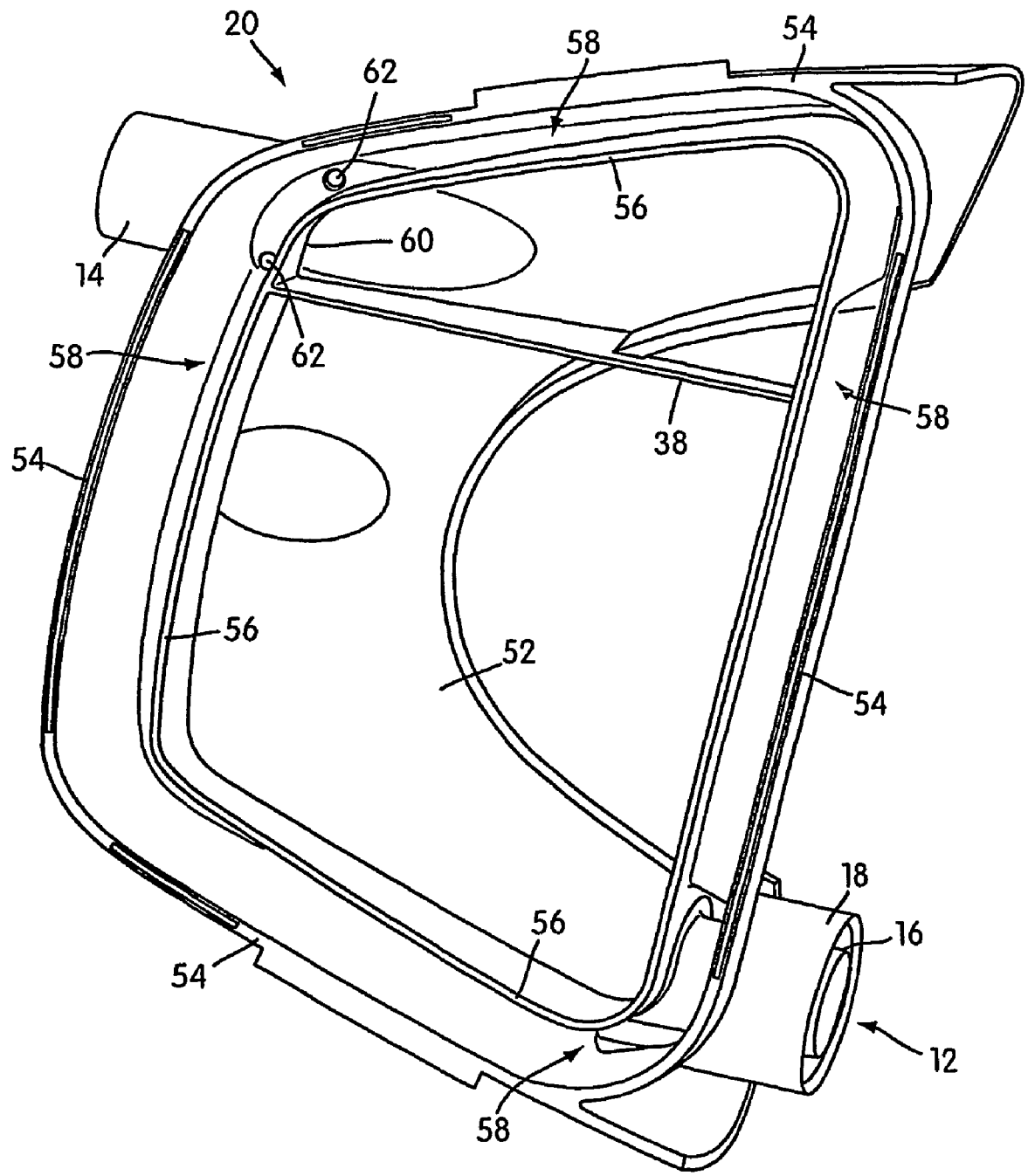
FIG. 3 is a bottom perspective view of a top cover of the humidifier shown in FIG. 1.

As shown in FIG. 3, an interior of the top cover 20 may include a divider wall structure 38 that is positioned corresponding to the channel structure 30 of the gasket 22. The interior of the top cover 20 may also be formed with an internal wall structure 56, discussed below. As also shown in FIG. 3, the humidifier inlet 12 includes a pair of concentric tubes, an inner tube 16 and an outer tube 18.

Figure 4:
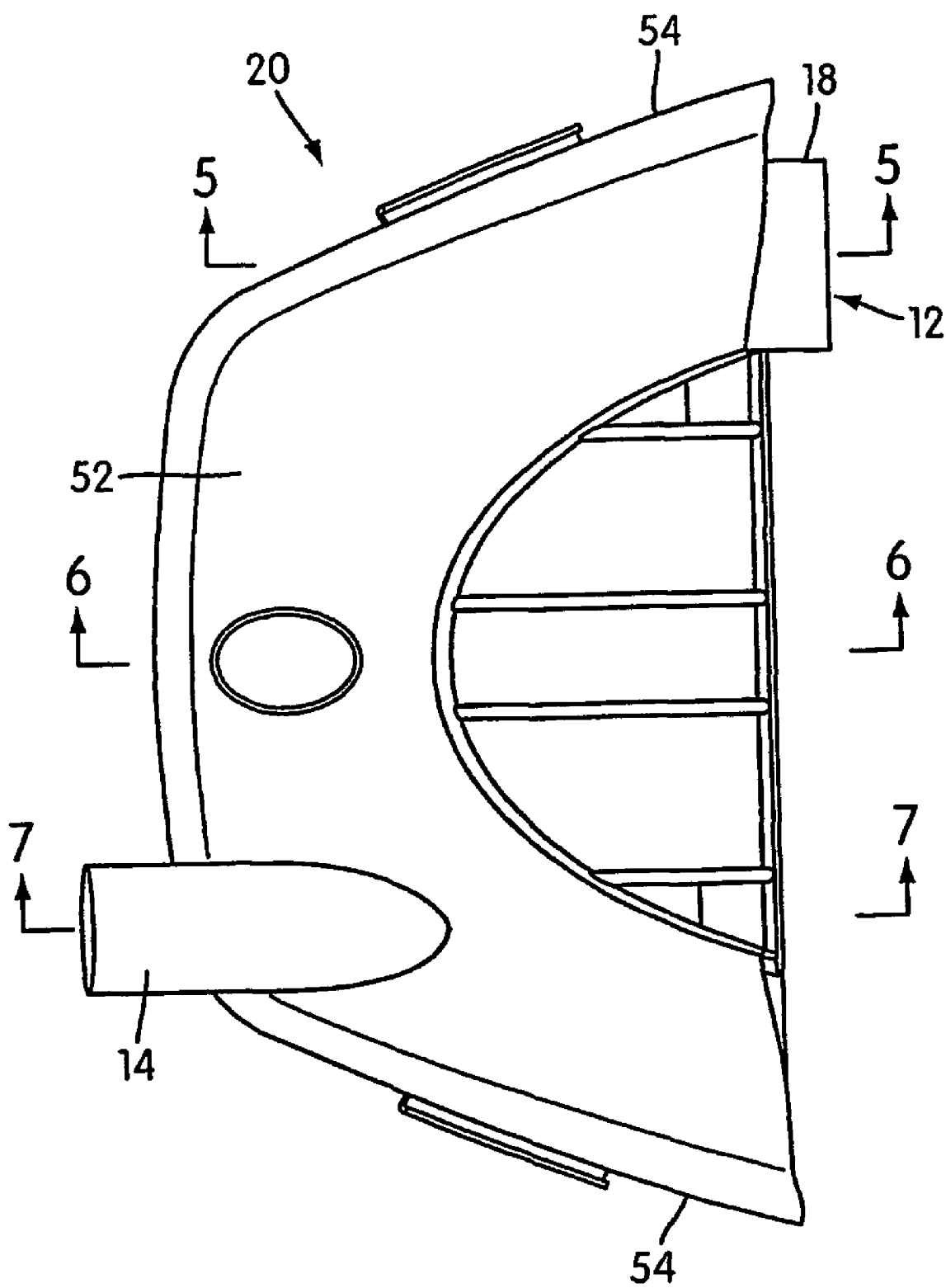
FIG. 4 is a top view of the top cover of the humidifier shown in FIG. 1.
Figure 5:
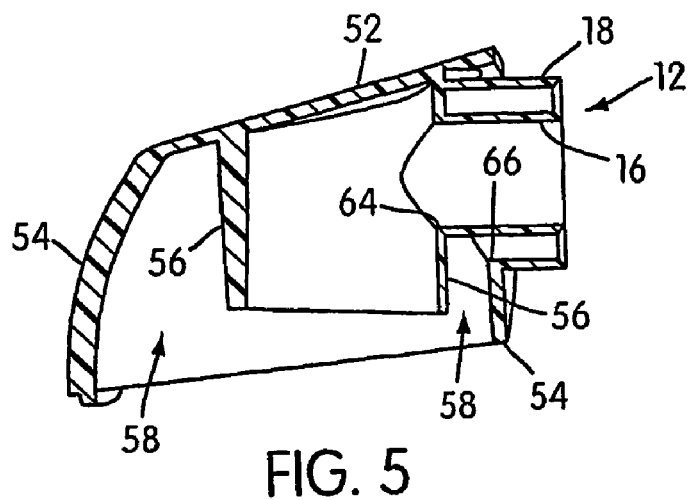
FIG. 5 is a cross-sectional view through line 5—5 of FIG. 4.
Figure 6:
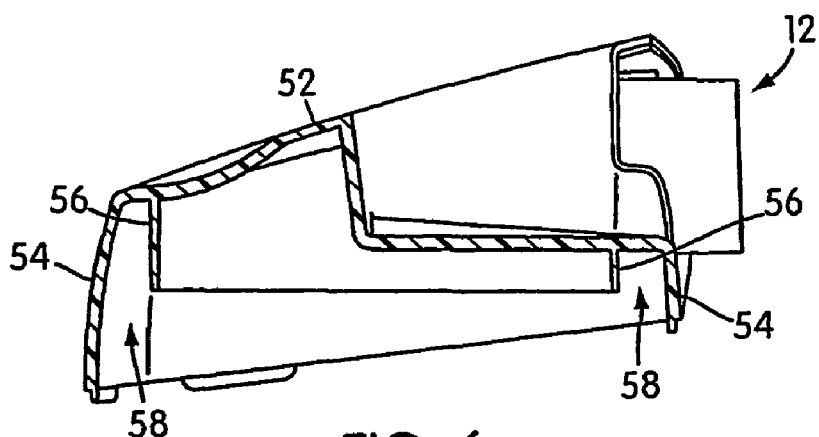
FIG. 6 is a cross sectional view through line 6—6 of FIG. 4.
Figure 7:
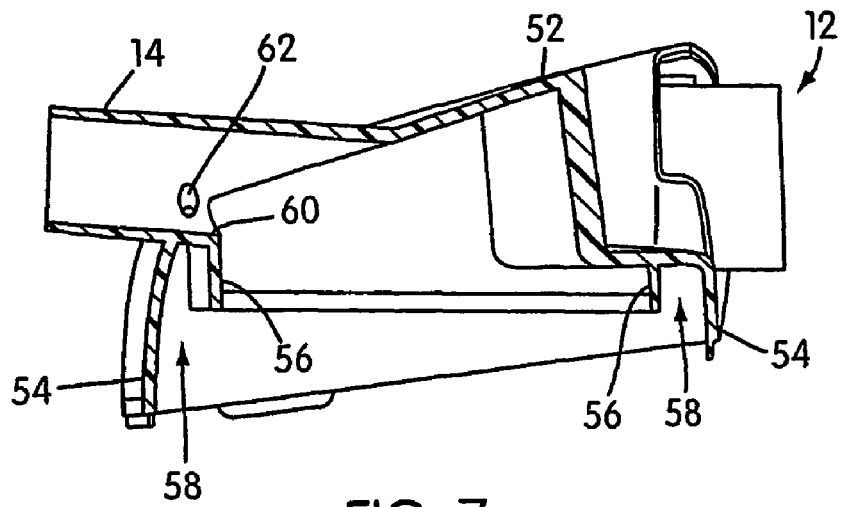
FIG. 7 is a cross-sectional view through line 7—7 of FIG. 4.

FIG. 4 illustrates a general arrangement of the inlet 12 and outlet 14 relative to the top cover 20. As shown, the inlet 12 and outlet 14 are disposed on opposite sides of the top cover 20 and at opposite ends thereof. Also, the inlet 12 and outlet 14 may be formed to extend generally parallel to one another. However, the inlet 12 and outlet 14 may alternatively be formed in any other relative arrangement. The top cover 20 includes a top wall 52, side walls 54 extending generally downwardly from the top wall 52, and the internal wall structure 56 also extending downwardly from the top wall 52. As shown in FIGS. 5 and 6, the internal wall structure 56 is generally parallel to and spaced inwardly from the side walls 54 to define a space 58 therebetween. Referring to FIG. 5, the inner tube 16 of the inlet 12 extends through the space 58 and provides an opening 64 within the internal wall structure 56 so as to be communicated with the interior of the humidifier 10. The outer tube 18 may be coaxial with and may surround the inner tube 16. The outer tube 18 provides an opening 66 within the side wall 54 and communicates with the space 58. In lieu of the concentric tubes 16, 18, it is also contemplated that the inlet 12 may be provided with a pair of inlet tubes, which communicate with the interior of the humidifier 10 and space 58, respectively, that are not concentric with one another. For example, it is contemplated that the inlet tubes may be arranged in a parallel, side-by-side manner, or any other suitable manner. It is also contemplated that the inlet tubes may be integrally formed, mechanically fastened to one another, or completely separate components. As shown in FIG. 7, the humidifier outlet 14 extends through the space 58 and provides an opening 60 within the internal wall structure 56. At least one aperture 62 is formed in the outlet tube 14 in a location between the side walls 54 and the internal wall structure 56, and is thus in communication with the space 58

Figure 8:
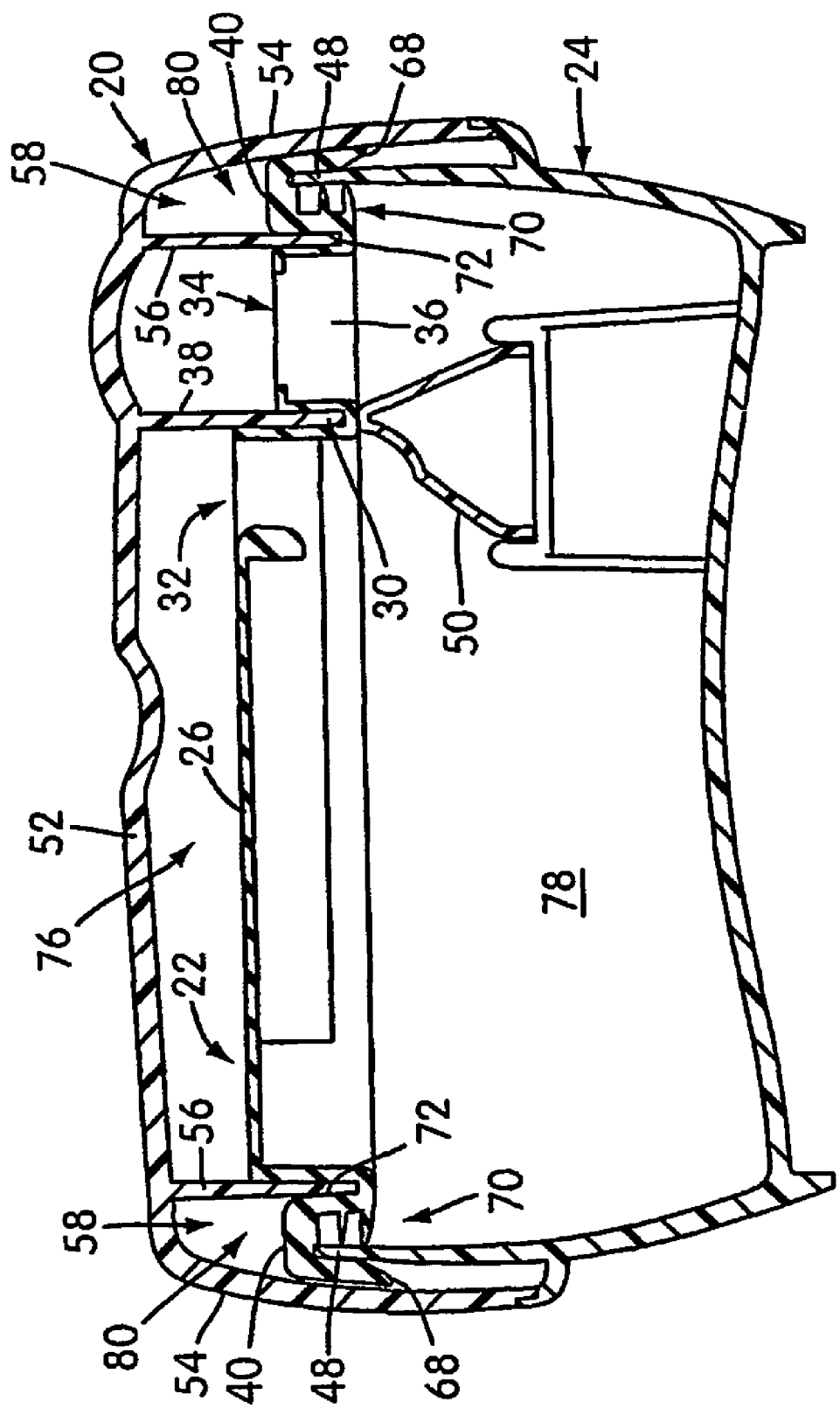
FIG. 8 is a front perspective partial sectional view of the assembled humidifier shown in FIG. 1.

As shown in FIG. 8, the gasket 22 is formed with a ledge receiving channel 68, which is defined on an outer side thereof by sealing flange 40. The ledge receiving channel 68 engages an exterior side of the ledge portion 48. The channel 68 also includes a plurality of sealing lips 70 that are configured to resiliently engage an interior surface of the ledge portion 48. Engagement of the flange 40 and lips 70 provides a resilient sealing connection between the gasket 22 and base 24. As also shown, the bridge structure 50 serves to intermediately support the gasket 22. In particular, a downwardly facing surface of the channel structure 30 is vertically supported on an upwardly facing surface of the bridge structure 50.

To assemble the humidifier 10, the gasket 22 is attached to the base 24, such that the ledge portion 48 is received within the flange 40. The top cover 20 is brought into engagement with the gasket 22, such that the internal wall structure 56 is received within a wall receiving channel 72 in the gasket 22. The internal wall structure 56 is engaged within the channel 72, thereby forming a resilient sealing connection with the gasket 22 and effectively enclosing space 58. Additionally, the dividing wall structure 38 is received within the channel 30. As discussed above and shown in FIG. 1, the top cover 20 is then secured to the base 24, e.g., via sliding clips 74 on either side of the top cover 20, to ensure that the top cover 20 and base 24 remain together when the air within the humidifier is at a higher pressure than ambient pressure.

Figure 9:
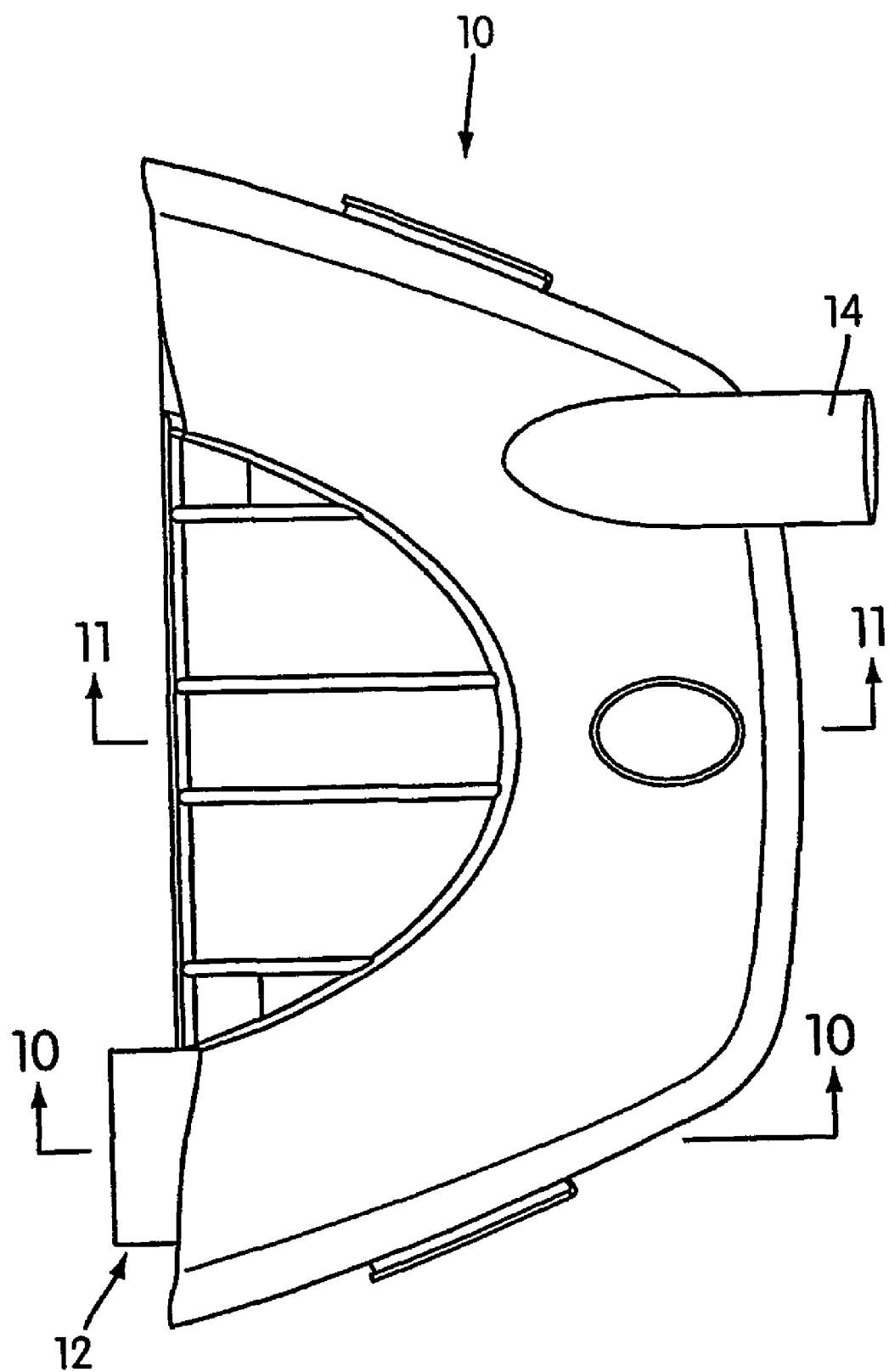
FIG. 9 is a top view of the assembled humidifier shown in FIG. 1.
Figure 11:
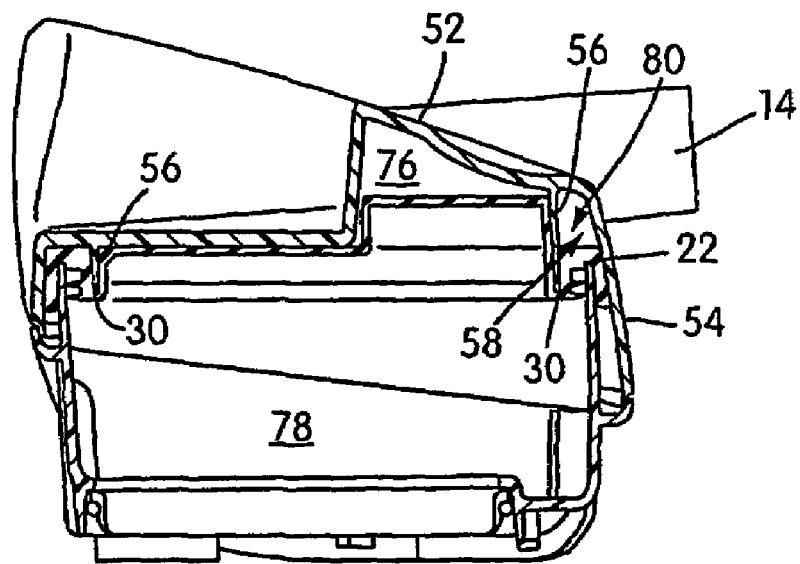
FIG. 11 is a cross-sectional view through line 11—11 of FIG. 9.
Figure 10:
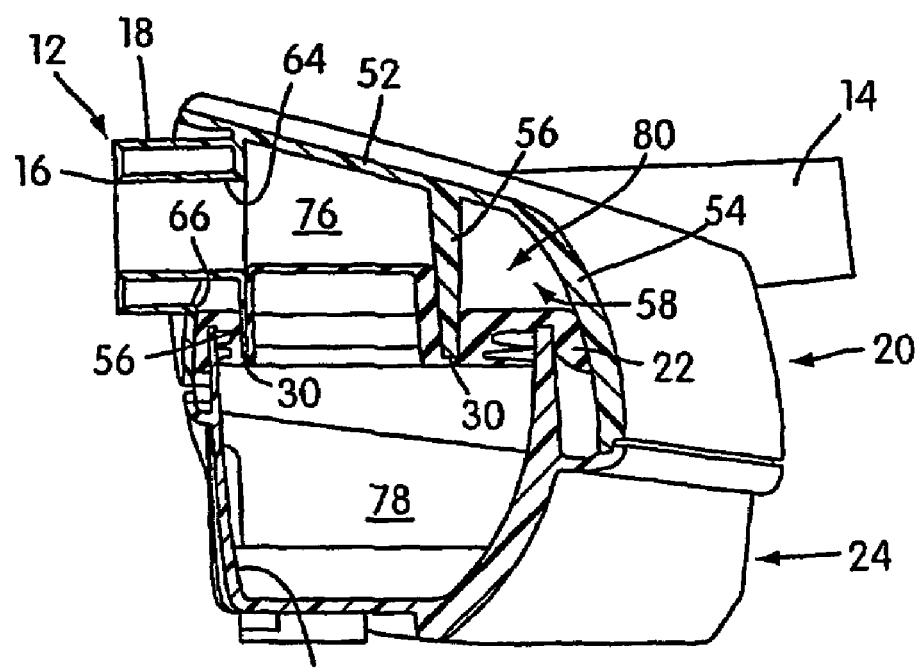
FIG. 10 is a cross-sectional view through line 10—10 of FIG. 9.

FIG. 9 is a top view of the assembled humidifier 10. FIGS. 10 and 11 are sectional views of the assembled humidifier 10 shown in FIG. 9. As shown in FIG. 10, an upwardly facing surface of the first section 26 of the gasket 22, a portion of the top wall 52, the divider wall structure 38, and portions of the internal wall structure 56 together define an upper chamber 76. The receptacle 42 of the base 24 together with a downwardly facing surface of the gasket 22 define a lower chamber 78. Referring back to FIG. 8, the upper chamber 76 is in communication with the inner tube 16 of the inlet 12 and the lower chamber 78 is in communication with the outlet 14 via the second apertures 34. The upper chamber 76 and the lower chamber 78 are in communication with each other via the first aperture 32. As shown in FIG. 11, the space 58 is thus sealed by the gasket 22 to form an internal passage 80. The internal passage 80 is thus defined by cooperating surfaces of the top wall 52, side walls 54, gasket 22, and the internal wall structure 56.

Figure 12:
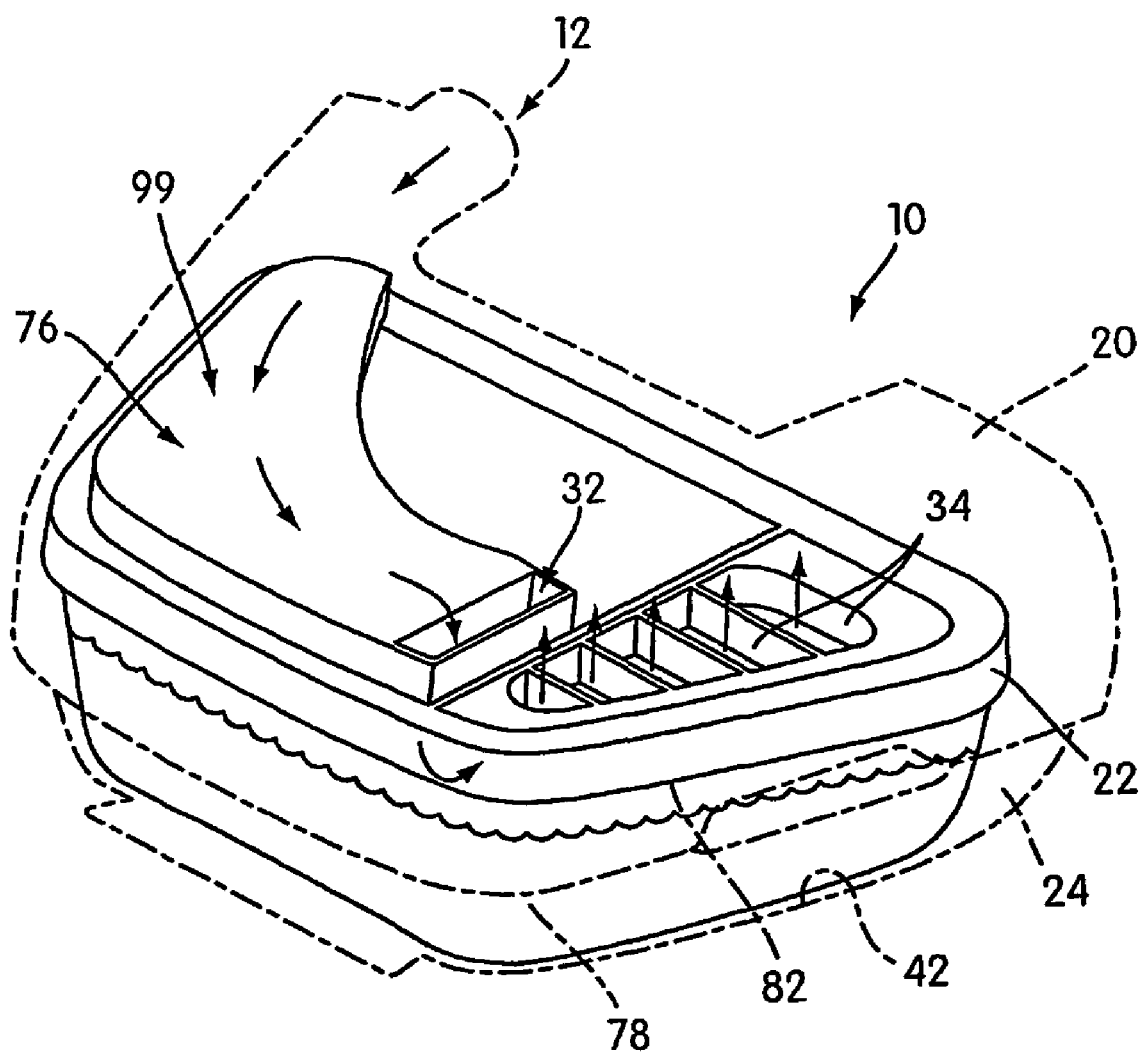
FIG. 12 is a perspective view of the humidifier schematically showing the direction of travel of breathable gas from the blower through the humidifier.

In use, a predetermined maximum volume of water, indicated at 82 in FIG. 12, is poured into the receptacle 42 of the base 24, e.g., after removing the top cover 20 and the sealing gasket 22. The top cover 20 and the sealing gasket 22 are reattached to the base 24 after filling the receptacle 42. In this manner, the volume of water 82 is held in the lower chamber 78. Air from the blower enters via the inner tube 16 of the inlet 12 and travels along the upper chamber 76 and into the first aperture 32. The air enters the lower chamber 78 where it is humidified by contact with the water, before exiting through apertures 34 in the gasket 22, and then out through outlet 14. It is contemplated that the inlet tube 16, the first chamber 76, the aperture 32, the second chamber 78, the second apertures 34, and the outlet 14 effectively define an internal fluid passage, indicated at 99 in FIG. 12, by which the breathable gas flows through the humidifier 10.

The outer tube 18 is connected to a monitoring conduit in the NIPPV or CPAP apparatus for communication with a sensing device (e.g., pressure transducer, microphone, etc.) in the NIPPV or CPAP apparatus. The aperture 62 (FIG. 3) and the internal passage 80 (FIGS. 10 and 11) thus provide communication between the outlet 14 and the sensing device, which allows for monitoring of parameters of the flow of breathable gas between the mask and outlet 14, such as pressure and/or noise levels thereof. A correction factor which allows for a degree of signal attenuation within the supply conduit between the mask and outlet 14 may be used to estimate an actual signal level at the mask based on the level of the parameter sensed at outlet 14 and the flow delivered by the flow generator. The sensing device is associated with the NIPPV or CPAP apparatus blower for increasing or decreasing the output of the blower to the humidifier, as required. Thus, the parameter of the breathable gas flow at the humidifier outlet 16 during use can be monitored and the blower output can be adjusted as required. Additionally, the humidifier outlet can be monitored without signal attenuation from the volume of water within the humidifier and/or the internal configuration of the humidifier and without inconvenient extra components.

It is contemplated that the at least one aperture 62 may be provided by a pair or more of apertures in the outlet tube 14 to decrease likelihood of a water droplet from the humid air blocking a single aperture. The humidifier 10 is formed with the upper and lower chambers 76 and 78 to provide spill protection for the humidifier 10 as described in co-pending Applications incorporated above, as well as co-pending application No. WO 02/066,107A1, entitled "A Humidifier", filed on even date herewith and hereby incorporated by reference in its entirety.

A particular advantage of the preferred embodiment is convenience and usability. Patients who may have poor dexterity, and clinicians are not burdened with manipulating small tubing. Further, cleaning and disinfection are also easier, because substantially the entire interior of the internal passage 80 is exposed when the humidifier is opened (i.e., when top cover 20 and gasket 22 are separated from each other). It is contemplated that materials for construction of the top cover 20, the gasket 22 and the base 24 may be chosen so as to enable various disinfecting or sterilizing methods to be used such as steam autoclaving, chemical cleaning and gamma ray sterilizing.

Additionally, the integral nature of the internal passage 80 significantly reduces componentry of the humidifier, which reduces manufacturing costs of the humidifier. This is particularly relevant when the top cover 20, gasket 22, and base 24 are formed from molded polymer materials, such as described above. The humidifier also provides for relatively simplistic assembly and disassembly. The ease of assembly provides further manufacturing cost savings, since there is very little time involved in assembling the components of the humidifier. Prior art humidifiers, which require use of mechanical fasteners, adhesives, connection of fittings and/or additional tubing may have substantially increased manufacturing costs. The ease of assembly and disassembly may also be advantageous for end users, such as patients and clinicians who regularly disassemble and assemble the humidifier, such as to fill and/or clean it, as discussed above.

In the illustrated embodiment, the humidifier 10 has a generally trapezoidal shape. It is contemplated that the humidifier 10 may also be configured with any other suitable shape, such as rectangular or semi-circular. It is also contemplated that the humidifier 10 may have any suitable dimensions. For example, the humidifier 10 may be configured with a height of about 9 cm, a width of 14 cm to 18 cm and a depth of about 12 cm. The outlet 14 may have an inner diameter of about 2 cm. The apertures 62 in the outlet 14 may have a diameter of about 2 mm. The inlet 14 may have an inner diameter of about 1.8 cm and the outer tube 18 may have an inner diameter of about 3 cm. The passage 80 may have an approximately rectangular section with a height of about 1 cm to 3 cm.

As mentioned, the outlet 14 is connectable with an outlet conduit having a patient mask at one end. In an alternative embodiment, the passage 80 may be in communication with the humidifier outlet 14 at the patient mask via a third conduit, rather through apertures 62. The third conduit can be integral with the outlet conduit or separate thereto. The third conduit may be internal or external of the outlet conduit.

Although preferred forms of the present invention have been described, it will be apparent to persons skilled in the art that modifications to the above embodiments can be made. For example, the present invention can be used in a humidifier which does not include the gasket 22. In such an embodiment, the passage 80 may be formed by having the internal protrusion 56 extending from the top wall 52 to the bottom wall 42 of the base 24. In another alternative embodiment, one of the internal walls of the passage 80 can be formed by a curved wall of the top cover, rather than the top and side wall(s) thereof. As a further alternative, the internal protrusion can be L-shaped and attached to a humidifier wall to form the passage with the gasket. Also, the passage 80 does not have to extend about the entire periphery of the humidifier 10 and can only extend about at least part thereof.

Figure 13:
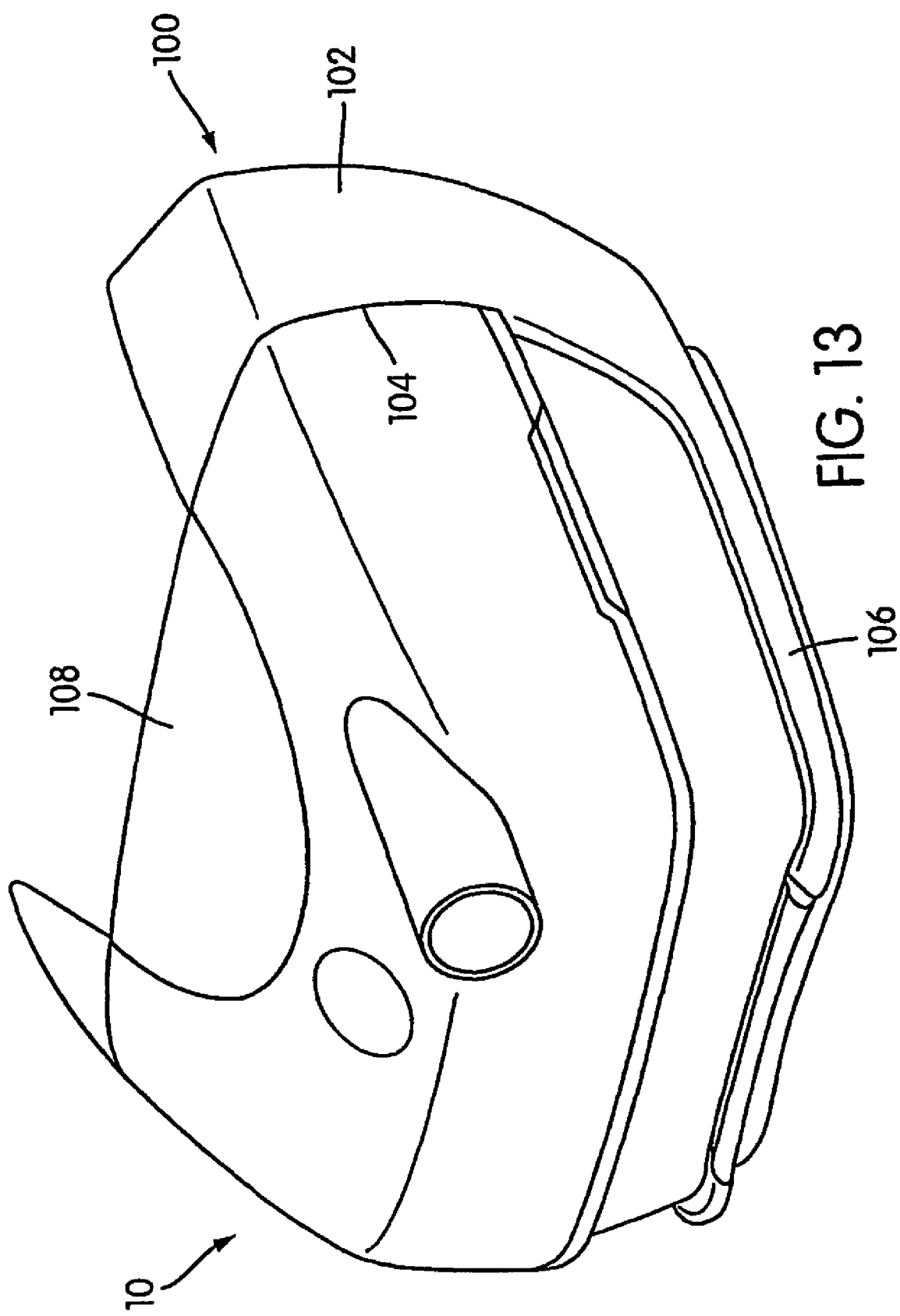
FIG. 13 is a perspective view of a humidifier and connecting structure according to another embodiment of the present invention.
Figure 14:
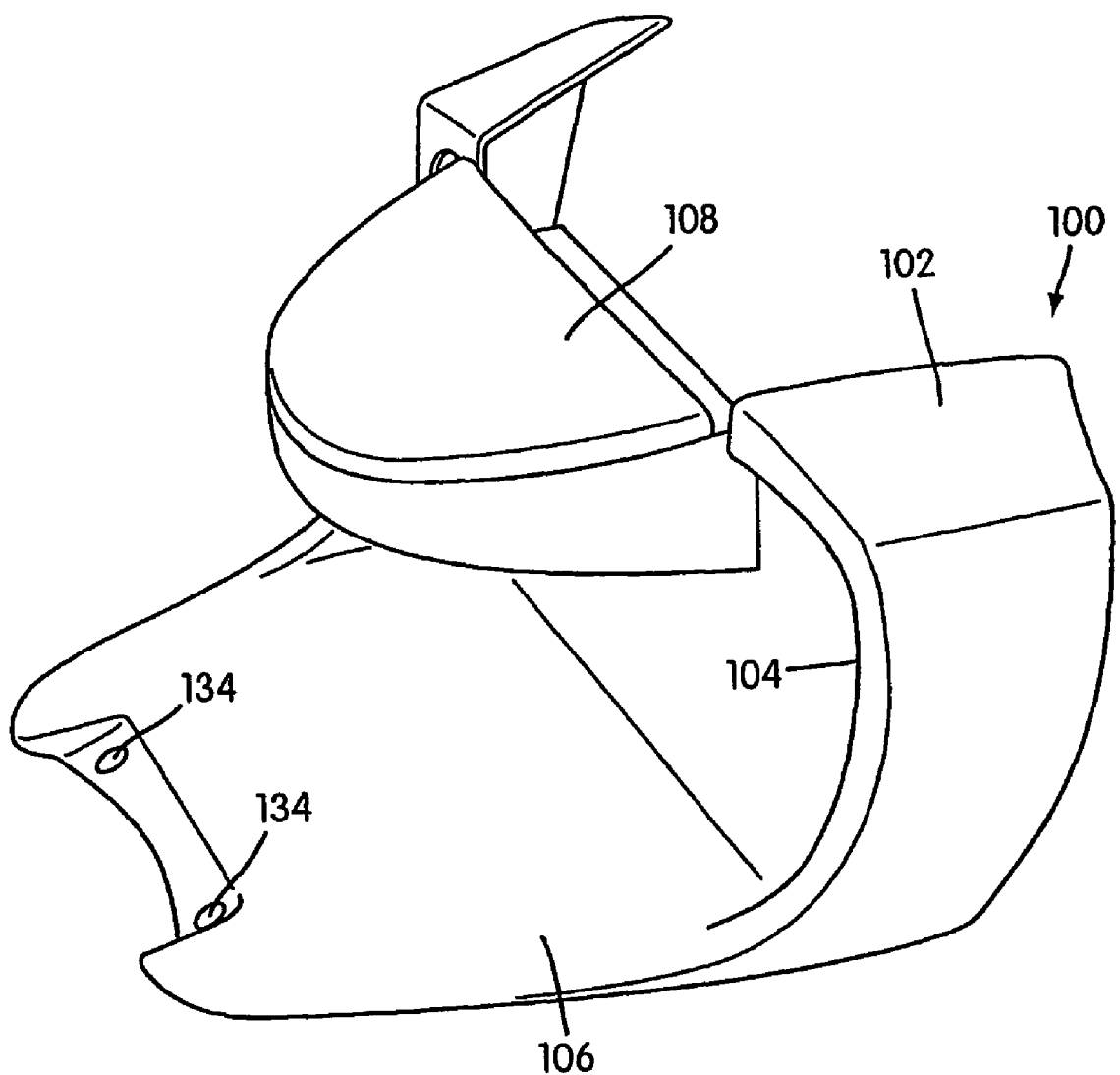
FIG. 14 is a perspective view of the connecting structure shown in FIG. 13.

It is contemplated that the humidifier 10 may be used as a retrofit or add-on component for a CPAP apparatus. To facilitate this usage, it may be preferable to provide an adapter or a connecting structure 100 (FIG. 13) that is configured to connect between the NIPPV or CPAP apparatus and the humidifier 10. As shown in FIG. 13, the connecting structure 100 includes a housing 102 that provides a generally horizontally extending receptacle 104 within which the humidifier 10 may be disposed. The housing 102 provides a base portion 106 that is configured to support the humidifier 10 thereon and a retaining portion 108 configured to secure the humidifier 10 in position. As shown in FIG. 14, the retaining portion 108 extends generally parallel to the base portion 106 and is spaced above the base portion 106. As discussed above, the humidifier 10 may be formed with the recess 110 (FIG. 1) that is open and of a complimentary shape to receive the retaining portion 108 therein. A forward portion of the base portion 106 may include generally upwardly open recesses 134, which will be discussed further below.

Figure 15:
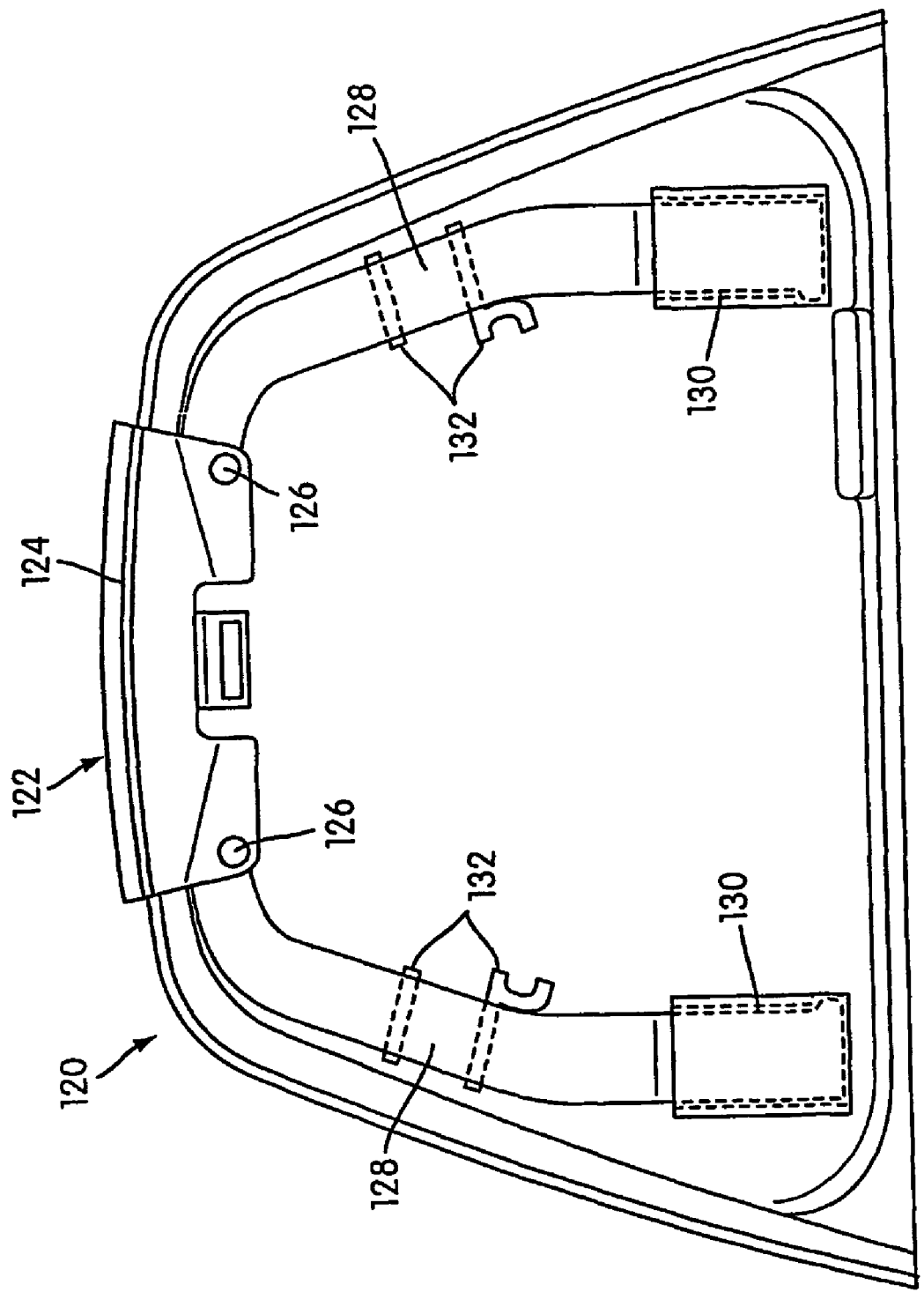
FIG. 15 is a bottom view of the humidifier shown in FIG. 13.

To facilitate connection of the humidifier 10 to the connecting structure 100, it is contemplated that another embodiment of a humidifier, indicated at 120 in FIG. 15, may include a securing mechanism 122. As shown, the securing mechanism 122 includes a resiliently biased pull member 124 that is formed with one or more locking lugs 126 extending generally downwardly therefrom. The pull member 124 is disposed at a forward end (assuming the rearward end of the humidifier 120 is adjacent the connecting structure 100) of the humidifier 120 and is resiliently biased by a pair of resilient legs 128. Rearward portions of the legs 128 are relatively securely retained within corresponding pocket structures 130 provided on a bottom side of the humidifier 120. Ribs 132 extend downwardly from the bottom side of the humidifier 120 and engage an intermediary portion of the legs 128 to define a space between the resilient legs 128 and the bottom side of the humidifier 120. In this manner, the pull member 124 is biased generally downwardly by the resilient legs 128, but may be manually moved (e.g., pulled) upward against a resilient bias of the legs 128.

As discussed above, the base portion 106 may include the generally upwardly open lug receiving recesses 134 (FIG. 14) within which the lugs 126 may be disposed when the humidifier 120 is disposed within the receptacle 104. As the humidifier 120 is inserted within receptacle 104, the legs 128 resiliently bias the lugs 126 into recesses 134. The lugs 126 and recesses 134 thereby secure the humidifier 120 within the receptacle 104. To remove the humidifier 120 from the receptacle 104, the pull member 124 is pulled upwardly to withdraw the lugs 126 from the recesses 134. The humidifier 120 may then be pulled generally horizontally out of the receptacle 104.

Figure 16:
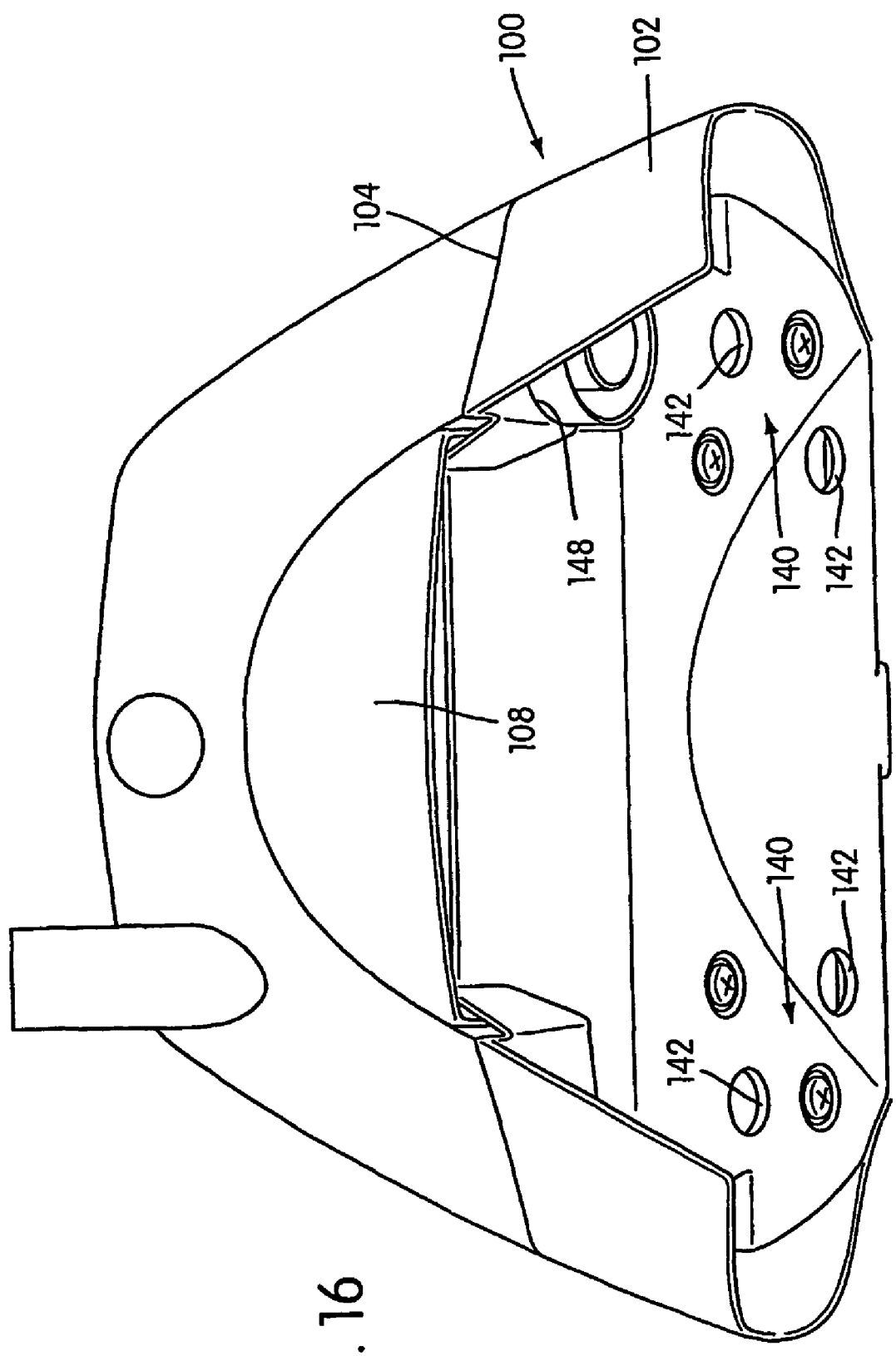
FIG. 16 is a rear perspective view of the humidifier and connecting structure shown in FIG. 13.
Figure 17:
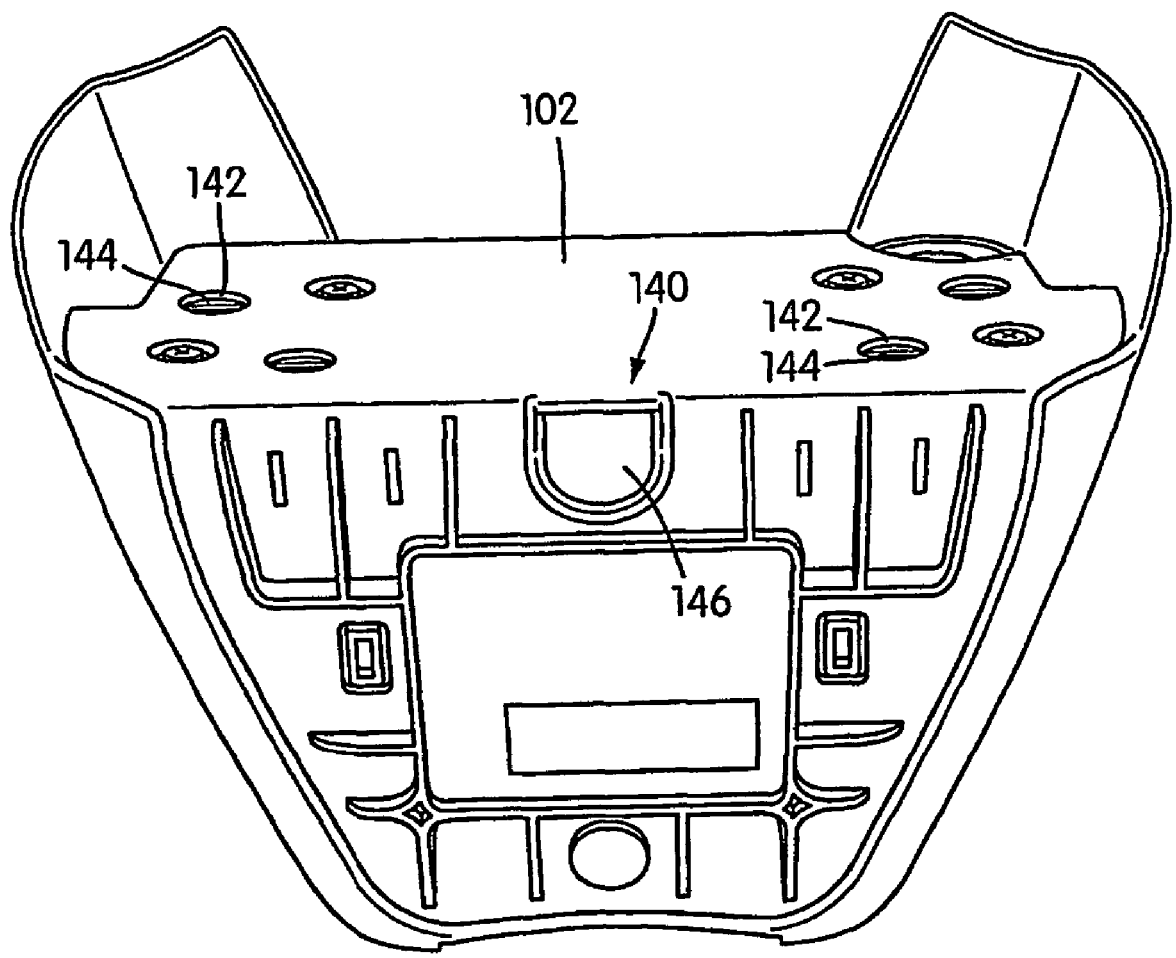
FIG. 17 is a bottom perspective view of the connecting structure shown in FIG. 13.

FIG. 16 shows a rearward side of the connecting structure 100. The rearward side of the connecting structure 100 provides a retaining mechanism 140 to secure the connecting structure 100 to the CPAP apparatus. The retaining mechanism 140 may include a series of apertures 142 within the rearward portion of the housing 102. The apertures 142 may receive therein, for example, prongs or tabs (not shown) provided by the NIPPV or CPAP apparatus. As shown in FIG. 17, within each aperture 142, a locking member 144 may be provided that is resiliently biased toward a position that partially encloses the respective aperture 142. As also shown in FIG. 17, a button structure 146 may be coupled to the locking members 144, such that manual movement of the button structure 146 moves the locking members 144 out of their biased positions to substantially fully open the apertures 142. It is contemplated that the tabs or prongs on the CPAP apparatus are provided with a groove therein such that when positioned within the apertures 142, the locking members 144 engage within respective grooves to thereby securely and detachably retain the connecting structure 100 to the CPAP apparatus.

Referring back to FIG. 16, the housing 102 of the connecting structure 100 may be provided with an opening 148 that allows the inlet 12 of the humidifier to extend therethrough so as to be connected to the CPAP apparatus.

Figure 18:
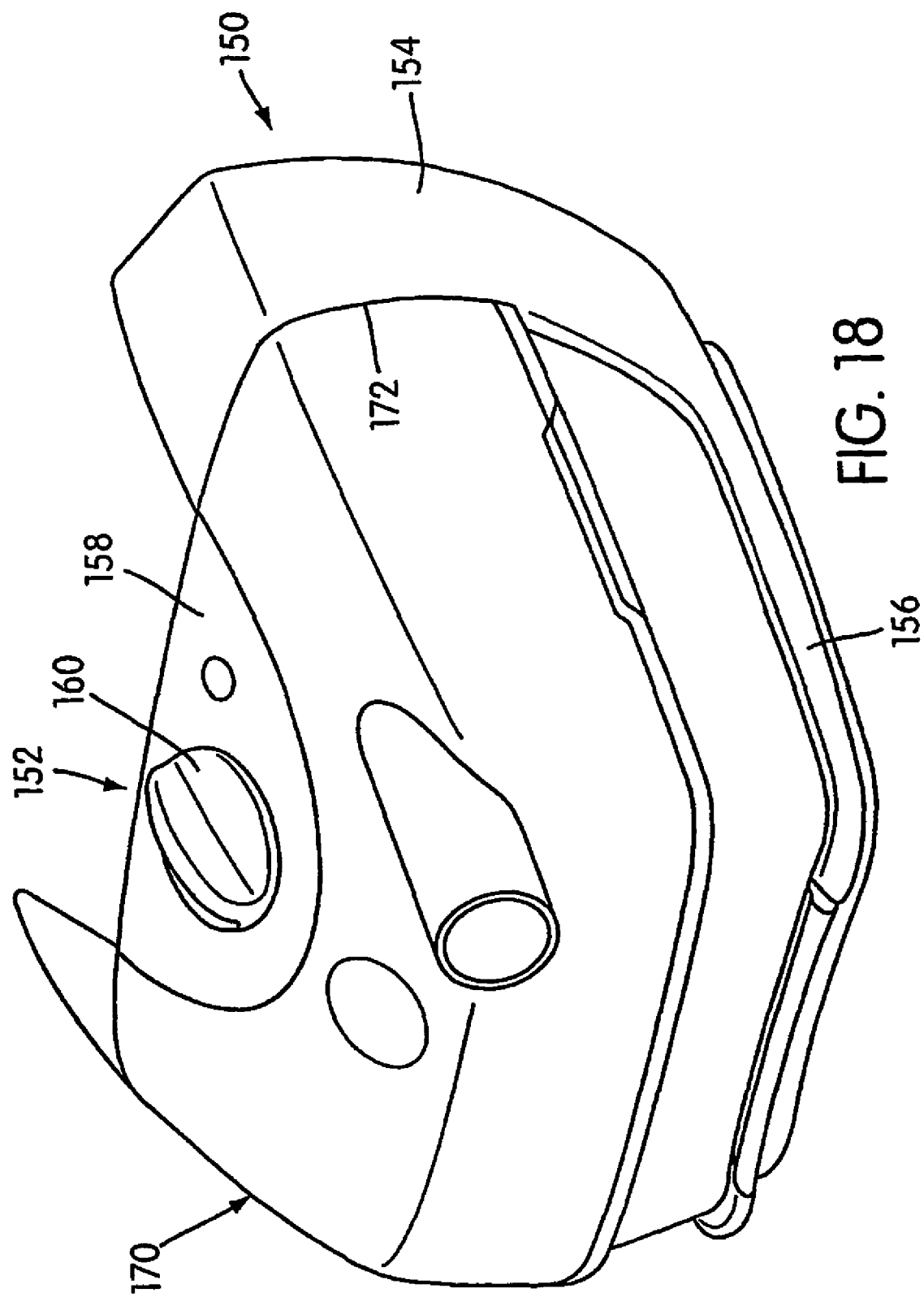
FIG. 18 is a perspective view of a humidifier and heater according to another embodiment of the present invention.

As discussed previously, in certain circumstances, it may be desirable to provide heated humid air to the respirator mask. Accordingly, another embodiment of the connecting structure, indicated at 150 in FIG. 18, may include a heater 152. The connecting structure 150 may include a housing 154 that provides a base portion 156 and retaining portion 158, similar to the housing 102 described above. As shown in FIG. 18, the retaining portion 158 may include a controller such as a knob or other selecting device 160 thereon to control a heat setting of the heater 152. It is also contemplated that the controller 160 may include a display device, such as an LCD screen.

Figure 19:
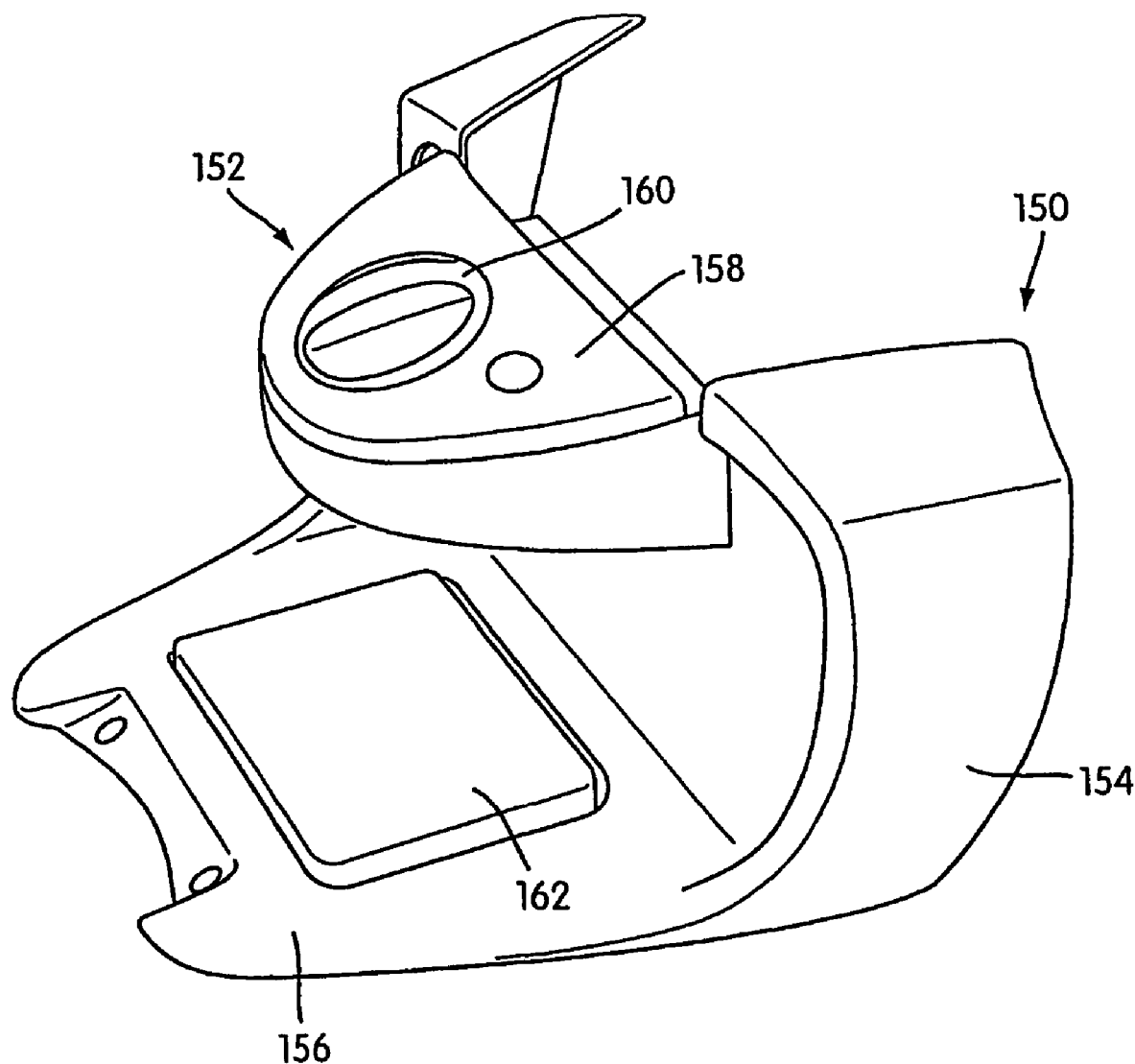
FIG. 19 is a perspective view of the heater shown in FIG. 18.

As shown in FIG. 19, the base portion 156 may include a heating element 162 thereon. The heating element 162 may be in the form of a substantially flat plate-like resistance heater, which heat generated thereby may be directly controlled by the controller 160.

As shown in FIG. 20, another embodiment of the humidifier is indicated at 170. The humidifier 170 is disposed within a receptacle 172 provided by the housing 154. It is contemplated that the humidifier 170 has the same basic construction as the humidifiers 10 and 120 described above. However, the humidifier 170 may include a heating plate 174 to facilitate heating of the liquid contained therein. In particular, an opening 176 is provided within a bottom wall 178 of the humidifier 170. The heating plate 174 is shaped to fit within the opening 176, as shown in FIG. 20. As shown in more detail in FIG. 21, the heating plate 174 includes an upstanding peripheral wall 180 which includes an outwardly extending peripheral lip 182. A resilient seal member 184 is disposed about an outer periphery of the peripheral wall 180 in contact with the peripheral lip 182. A ring-like retaining member 186 may be press fit onto the peripheral wall 180 to retain the seal 184 in position on the peripheral wall 180. The retaining member 186 includes an outwardly extending flange structure 188. The seal 184 is disposed between the peripheral lip 182 and flange structure 188. It is contemplated that the retaining member 186 may be press fit onto the heating plate 174, as described above, or may be formed in one piece therewith. The bottom wall 178 of the humidifier 170 is formed with an annular upstanding flange 190 which receives the heating plate 174. It is contemplated that the flange 190 may be slightly tapered inwardly in the upward direction to ease insertion of the heating plate 174. As shown, the flange 190 may include a generally horizontally extending lip structure 192 that vertically retains the heating plate 174.

Referring to FIGS. 19–21, with the humidifier 170 in position within the receptacle 172, a bottom surface of the heating plate 174 is in contact with an upper surface of the heating element 162. In this manner, a heat generated by the heating element 162 is conductively transferred to the heating plate 174. The liquid within the humidifier 170 is exposed to an upper surface of the heating plate 174 and conducts heat therefrom. It is contemplated that a temperature of the liquid within the humidifier 170 may be controlled by manipulation of the controller 160.

It is also contemplated that the heating element 162 may be upwardly resiliently biased to ensure adequate contact between the heating element 162 and the heating plate 174.

Figure 22:
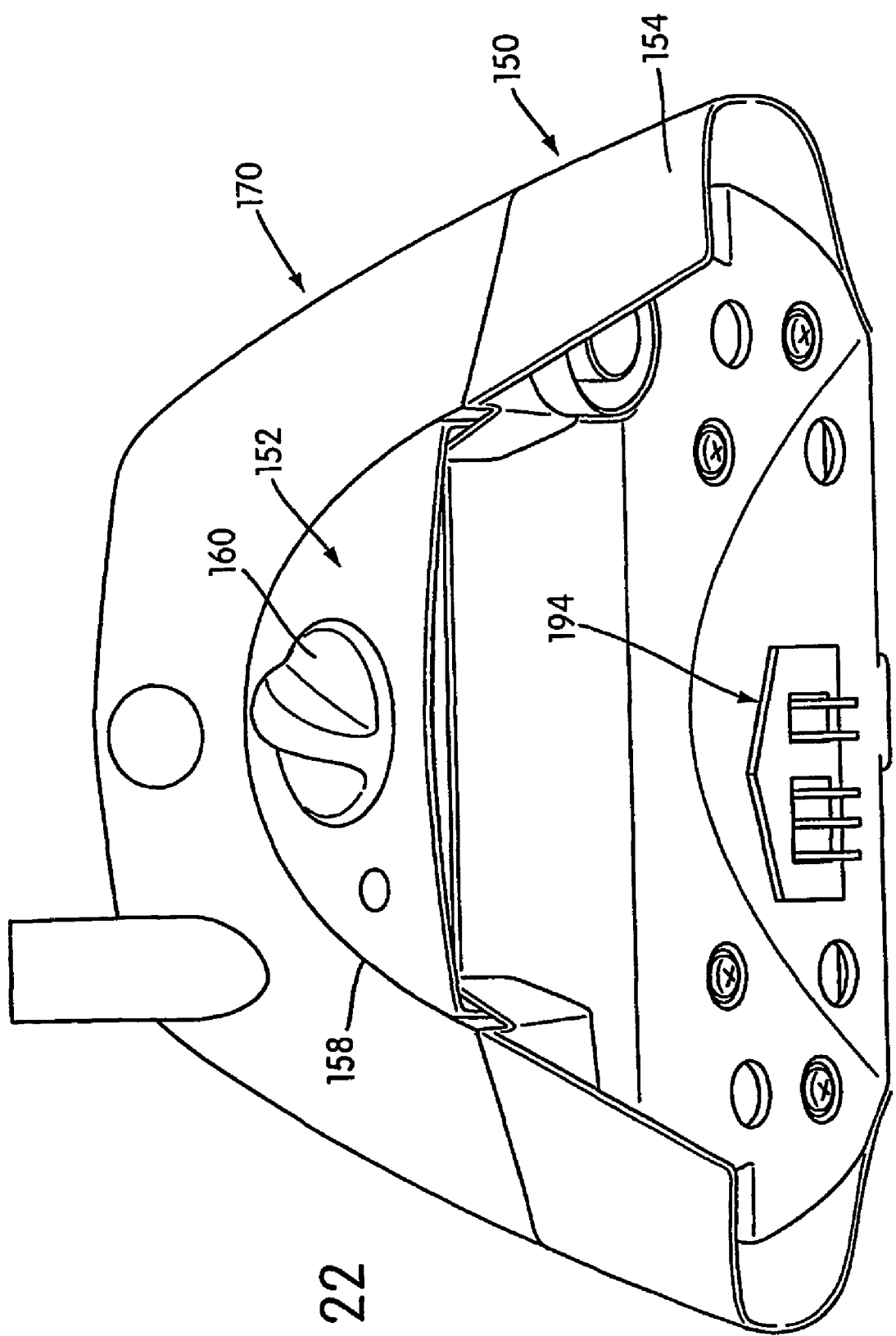
FIG. 22 is a rear perspective view of the humidifier and heater shown in FIG. 18.
Figure 23:
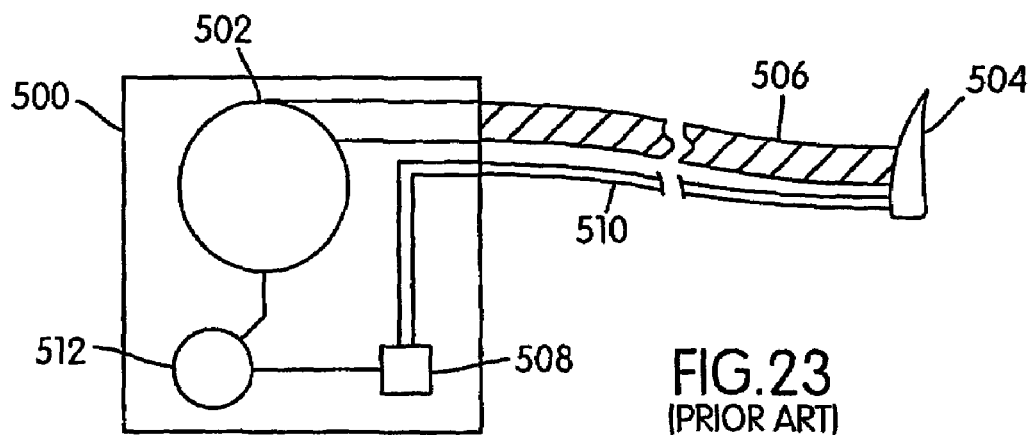
FIGS. 23–27 are schematic views of prior art CPAP apparatuses.
Figure 24:
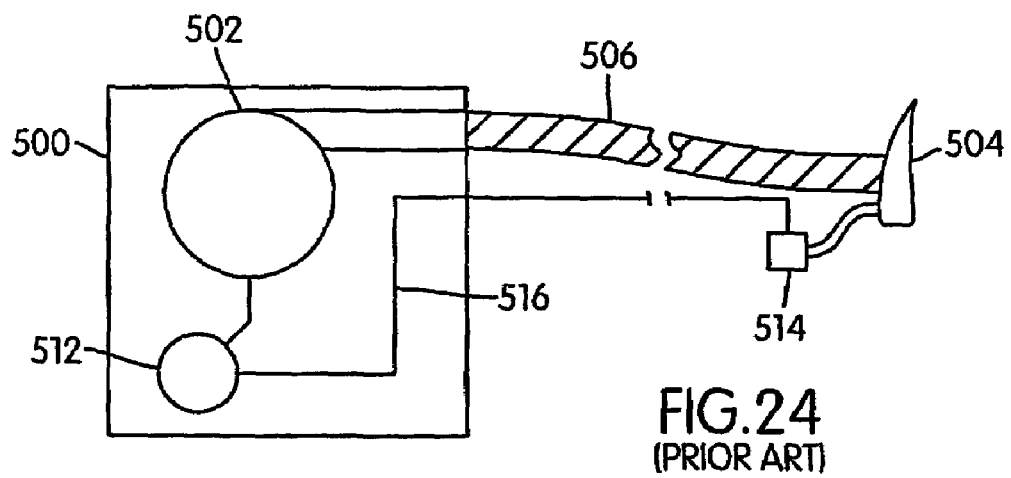
Figure 25:
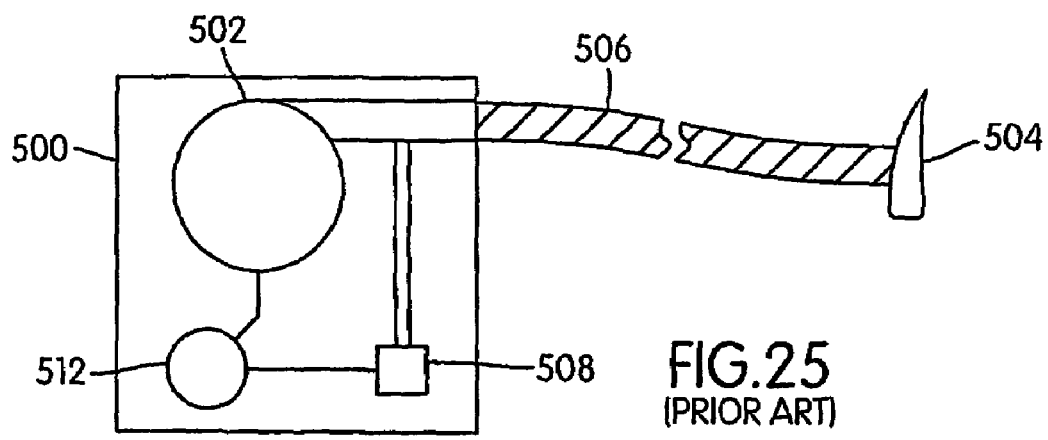
Figure 26:
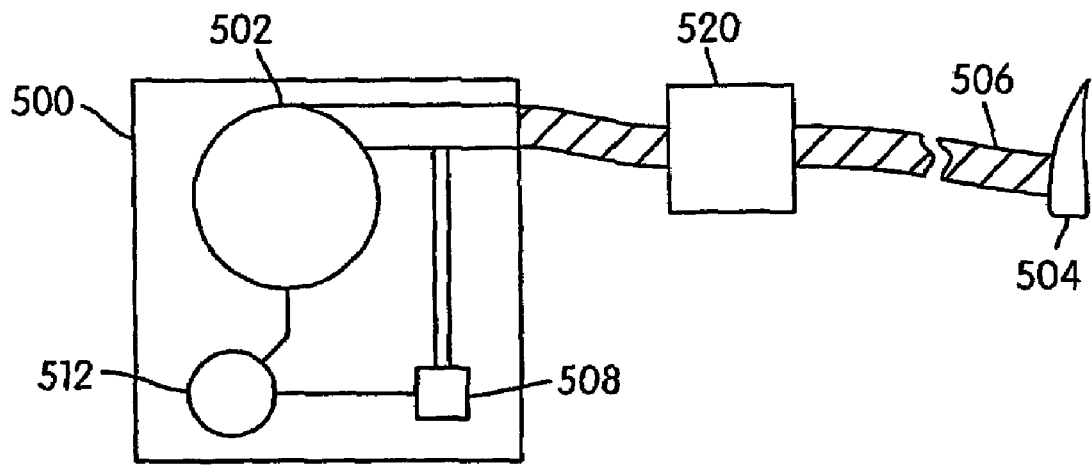
Figure 27:
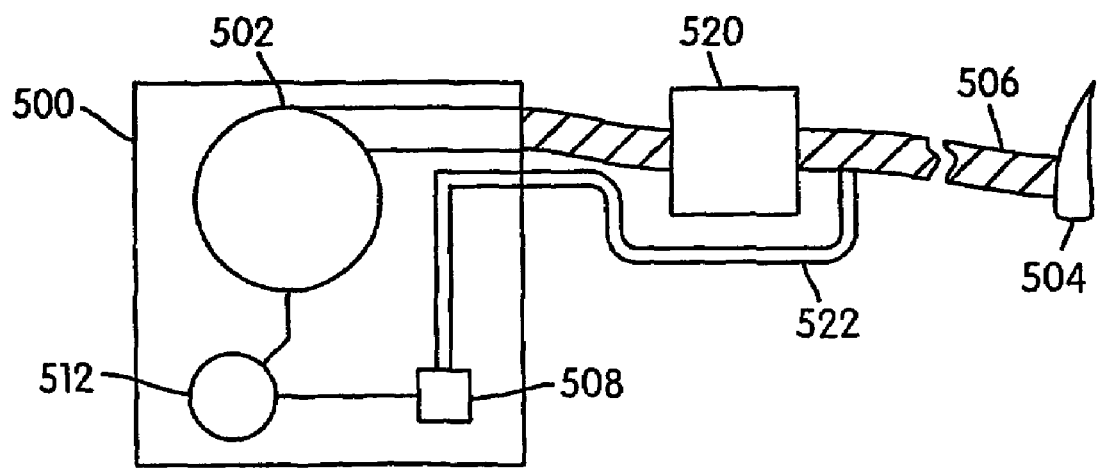
Figure 28:
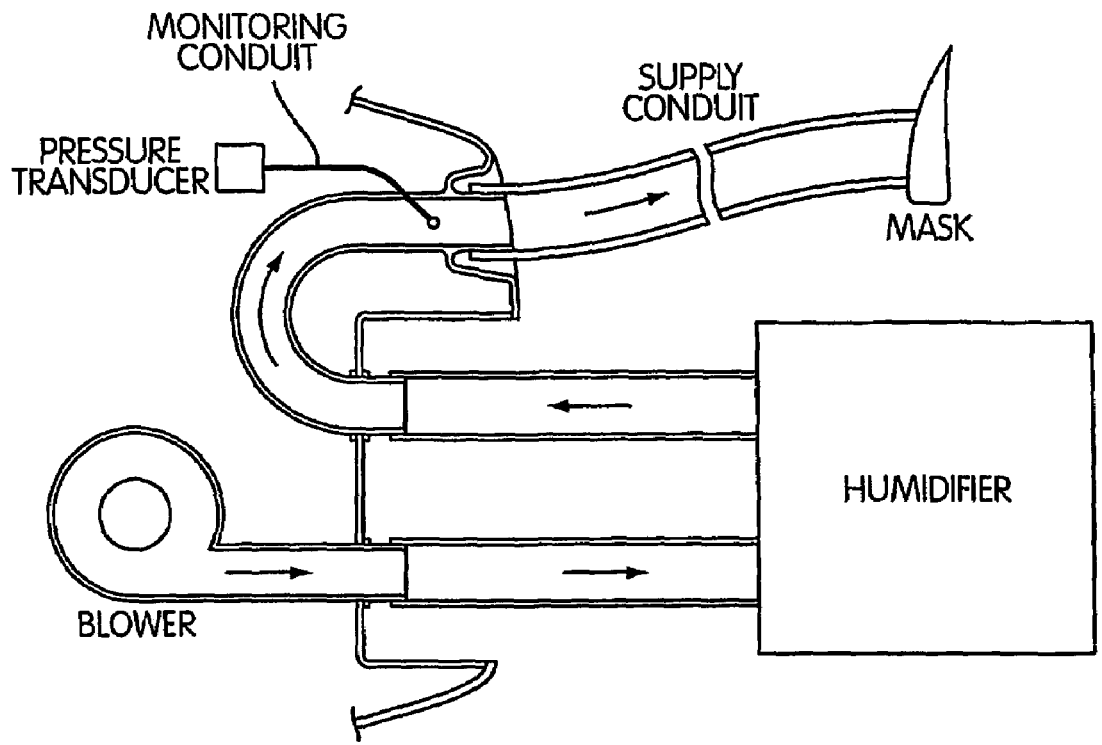
FIGS. 28–29 are schematic views of related art CPAP apparatuses.
Figure 29:
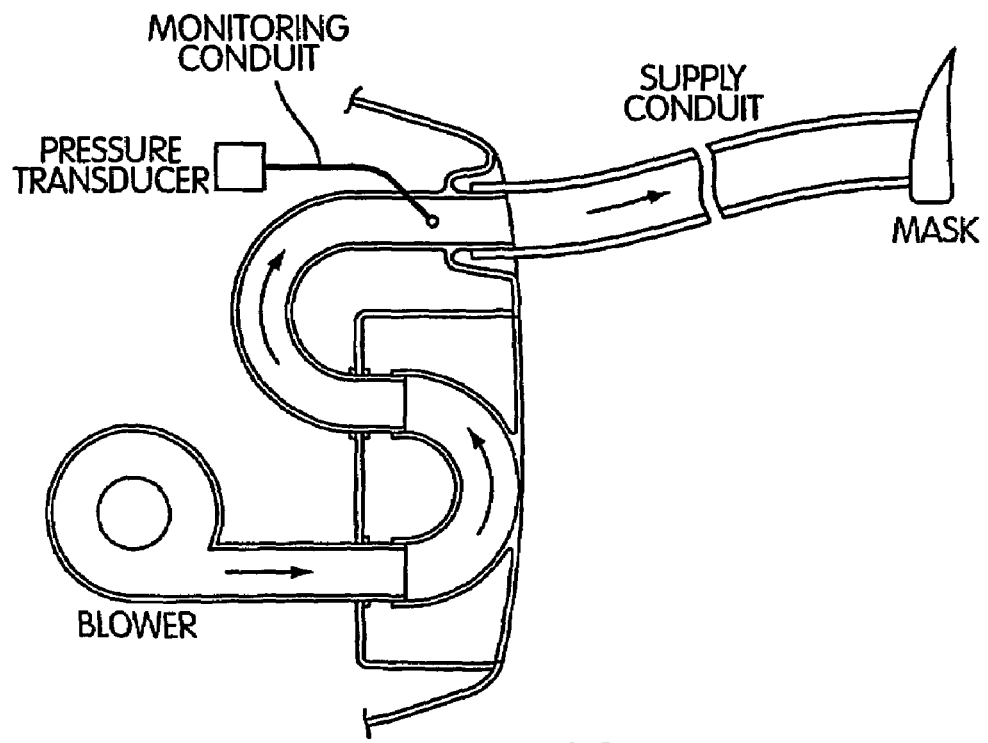

As shown in FIG. 22, a rearward portion of the connecting structure 150 may include a plurality of generally outwardly extending contact elements 194. It is contemplated that the contact element 194 may communicate with a power supply within the CPAP apparatus and/or a controller and/or sensors. In this manner, power may be delivered to the heater 152 directly from the CPAP apparatus. Additionally, a controller within the CPAP apparatus itself may control the heater 152. Furthermore, it is contemplated that sensors within the CPAP apparatus may monitor a heat output of the heater 152. Moreover, it may be possible for a CPAP apparatus to automatically adjust a heat output of the heater 152 based on a measured temperature thereof or of the water within the humidifier or of the breathable air exiting the humidifier.

The invention claimed is:

1. A humidifier comprising:
a first humidifier part,
a second humidifier part connectable with the first humidifier part, and
a sealing gasket disposed between the first and second humidifier parts;
wherein the second humidifier part is configured to hold a volume of liquid therein, the first and second humidifier parts and the sealing gasket define first and second internal passages within the humidifier, and the first passage is disposed so as to be exposed to a surface of the volume of liquid and the second passage being isolated from at least one of the first passage and the surface of the volume of liquid, the second passage being configured to communicate with a pressure and/or sound sensing device.

2. The humidifier according to claim 1, wherein the first and second humidifier parts are separable from one another in a manner such that walls of the first and second internal passages are substantially entirely exposed.

3. The humidifier according to claim 1, wherein a portion of an internal surface of the first humidifier part defines at least one internal wall of the second internal passage.

4. The humidifier according to claim 3, wherein the first humidifier part includes a top wall, a peripherally extending side wall extending downwardly from the top wall, and an internal wall structure extending downwardly from the top wall generally parallel to and inwardly spaced from the peripherally extending side wall, and the internal wall structure, portions of the top wall, and portions of the peripherally extending side walls define corresponding internal walls of the second internal passage.

5. The humidifier according to claim 4, wherein a portion of a surface of the sealing gasket defines a corresponding internal wall of the second internal passage.

6. The humidifier according to claim 1, wherein the first humidifier part includes first and second inlet tubes and an outlet tube, the first inlet tube and outlet tube being communicated with the first internal passage, and the second inlet tube and the outlet tube being communicated with the second internal passage.

7. The humidifier according to claim 6, wherein the outlet tube extends from the internal wall structure of the first humidifier part in such a manner to be communicated with the first internal passage to outside of the humidifier, and the second internal passage is communicated with the outlet tube via at least one aperture formed in the outlet tube.

8. The humidifier according to claim 7, wherein the at least one aperture is provided by a pair of apertures.

9. The humidifier according to claim 7, wherein the first inlet tube extends from the internal wall structure of the first humidifier part in such a manner to be communicated with the first internal passage to outside of the humidifier, and the second inlet tube extends from the peripherally extending side wall of the first humidifier part in such a manner to be communicated with the second internal passage to the aperture within the outlet tube.

10. The humidifier according to claim 9, wherein the second inlet tube is coaxial with and surrounds the first inlet tube.

11. The humidifier according to claim 1, wherein the first and second humidifier parts are formed from a relatively rigid polymer material and the sealing gasket is formed from a relatively resilient material.

12. The humidifier according to claim 1, further comprising a heater configured to raise a temperature of the volume of liquid within the humidifier.

13. The humidifier according to claim 1, wherein the first humidifier part includes an inlet having first and second inlet portions directed to the first and second internal passages, respectively.

14. The humidifier according to claim 13, wherein the first and second inlet portions are coaxial.

15. A CPAP apparatus including a humidifier according to claim 1.

16. A method of determining pressure within a conduit supplying breathable gas from a CPAP apparatus to a patient mask, the method comprising:
providing a humidifier with first and second internal passages therein, wherein the first passage is disposed within the humidifier so as to be exposed to a surface of a volume of liquid present within the humidifier and the second passage is isolated from the first passage;
supplying the breathable gas to a first inlet tube of the humidifier in communication with the first internal passage so that breathable gas flowing therethrough is humidified by contact with the volume of liquid and is communicated with an outlet tube of the humidifier;
providing an aperture within the outlet tube in communication with the second internal passage;
and measuring a pressure within the second internal passage to determine pressure within the outlet tube.

17. The method according to claim 16, further comprising forming at least a portion of the second internal passage in a top cover of the humidifier.

18. The humidifier according to claim 1, wherein the first humidifier part includes a top cover that defines at least a portion of the second internal passage.

19. A humidifier comprising:
a base;
a top cover connectable with the base;
a sealing gasket disposed between the base and the top cover; and
first and second internal passages within the humidifier, the first passage being disposed so as to be exposed to a surface of a volume of liquid within the base, and the second passage being at least partially formed in the top cover and being configured to communicate with a pressure and/or sound sensing device.

20. A humidifier comprising:

a first humidifier part, a second humidifier part connectable with the first humidifier part, and a sealing gasket disposed between the first and second humidifier parts;

wherein the second humidifier part is configured to hold a volume of liquid therein, the first and second humidifier parts and the sealing gasket define first and second internal passages within the humidifier and the first passage is disposed so as to be exposed to a surface of the volume of liquid and the second passage being isolated from at least one of the first passage and the surface of the volume of liquid, the second passage being configured to communicate with a pressure and/or sound sensing device, and wherein a portion of a surface of the sealing gasket defines a corresponding internal wall of the second internal passage.

21. A humidifier comprising:

a first humidifier part, a second humidifier part connectable with the first humidifier part, and a sealing gasket disposed between the first and second humidifier parts;

wherein the second humidifier part is configured to hold a volume of liquid therein, the first and second humidifier parts and the sealing gasket define first and second internal passages within the humidifier, and the first passage is disposed so as to be exposed to a surface of the volume of liquid and the second passage being isolated from at least one of the first passage and the surface of the volume of liquid, the second passage being configured to communicate with a pressure and/or sound sensing device, and wherein the first humidifier part includes an outlet tube that extends from an internal wall structure of the first humidifier part in such a manner to be communicated with the first internal passage to outside of the humidifier, and the second internal passage is communicated with the outlet tube via at least one aperture formed in the outlet tube.

22. The humidifier according to claim 19, wherein the second passage is isolated from at least one of the first passage and the surface of the volume of liquid.

23. The humidifier according to claim 19, wherein the top cover includes an inlet having first and second inlet portions directed to the first and second internal passages, respectively.

* * * * *

UNITED STATES PATENT AND TRADEMARK OFFICE
CERTIFICATE OF CORRECTION

PATENT NO.         : 7,137,388 B2
APPLICATION NO. : 10/467304
DATED              : November 21, 2006
INVENTOR(S)        : Virr et al.

It is certified that error appears in the above-identified patent and that said Letters Patent is hereby corrected as shown below:

Column 7, line 65, change "WO 02/066,107A1, entitled "A Humidifier" to:

--WO 02/066106 A1, entitled "Humidifier With Structure to Prevent Backflow of Liquid Through the Humidifier Inlet"--

Signed and Sealed this

Thirteenth Day of February, 2007

JON W. DUDAS
*Director of the United States Patent and Trademark Office*